US012773294B2

(12) United States Patent
Simoes et al.

(10) Patent No.: US 12,773,294 B2
(45) Date of Patent: Oct. 27, 2026

(54) MIXED REALITY-BASED SCREW TRAJECTORY GUIDANCE

(71) Applicant: Howmedica Osteonics Corp., Mahwah, NJ (US)

(72) Inventors: Vincent Abel Maurice Simoes, Locmaria Plouzané (FR); Florence Delphine Muriel Maillé, Locmaria Plouzané (FR); Sergii Poltaretskyi, Ependes FR (CH)

(73) Assignee: Howmedica Osteonics Corp., Mahwah, NJ (US)

( * ) Notice: Subject to any disclaimer, the term of this patent is extended or adjusted under 35 U.S.C. 154(b) by 245 days.

(21) Appl. No.: 17/923,179

(22) PCT Filed: Apr. 28, 2021

(86) PCT No.: PCT/US2021/029572
§ 371 (c)(1),
(2) Date: Nov. 3, 2022

(87) PCT Pub. No.: WO2021/225840
PCT Pub. Date: Nov. 11, 2021

(65) Prior Publication Data

US 2023/0346506 A1 Nov. 2, 2023

Related U.S. Application Data

(60) Provisional application No. 63/019,906, filed on May 4, 2020.

(51) Int. Cl.
*A61B 90/00* (2016.01)
*A61B 34/00* (2016.01)
(Continued)

(52) U.S. Cl.
CPC .............. *A61B 90/37* (2016.02); *A61B 34/10* (2016.02); *A61B 34/20* (2016.02); *A61B 34/25* (2016.02);
(Continued)

(58) Field of Classification Search
CPC ......... A61B 90/37; A61B 34/20; A61B 34/25; A61B 90/39; A61B 2090/107; A61B 2090/365; A61B 2090/3983
(Continued)

(56) References Cited

U.S. PATENT DOCUMENTS 6,856,324 B2 2/2005 Sauer et al.
8,160,325 B2 4/2012 Zug et al.
(Continued)

FOREIGN PATENT DOCUMENTS

CA 3001898 A1 4/2017
CA 3099718 A1 11/2019
(Continued)

OTHER PUBLICATIONS

"Aurora—The Aurora Electromagnetic Tracking System," NDI, Nov. 2013, 8 pp.
(Continued)

*Primary Examiner* — Jin Ge
(74) *Attorney, Agent, or Firm* — Shumaker & Sieffert, P.A.

(57) ABSTRACT

A method comprises determining, by a surgical assistance system, a potential insertion point on a surface of a bone of a patient; and presenting, by a Mixed Reality (MR) visualization device of the surgical assistance system, an MR scene that includes a virtual trajectory guide, wherein: the virtual trajectory guide comprises an elliptical surface, and for each location of a plurality of locations on the elliptical surface: the location corresponds to a potential insertion axis
(Continued)

that passes through the location and the potential insertion point on the surface of the bone, and the location is visually distinguished based on a quality of a portion of the bone along the potential insertion axis corresponding to the location.

24 Claims, 13 Drawing Sheets

(51) Int. Cl.
*A61B 34/10* (2016.01)
*A61B 34/20* (2016.01)

(52) U.S. Cl.
CPC ........ *A61B 90/39* (2016.02); *A61B 2034/107* (2016.02); *A61B 2090/365* (2016.02); *A61B 2090/3983* (2016.02)

(58) Field of Classification Search
USPC .......................................................... 345/633
See application file for complete search history.

(56) References Cited

U.S. PATENT DOCUMENTS

| | | | |
|---|---|---|---|
| 8,175,683 | B2 | 5/2012 | Roose |
| 8,231,634 | B2 | 7/2012 | Mahfouz et al. |
| 8,521,255 | B2 | 8/2013 | DiSilvestro et al. |
| 8,532,807 | B2 | 9/2013 | Metzger |
| 8,634,618 | B2 | 1/2014 | Zug et al. |
| 8,870,889 | B2 | 10/2014 | Frey |
| 9,097,890 | B2 | 8/2015 | Miller et al. |
| 9,198,678 | B2 | 12/2015 | Frey et al. |
| 9,220,570 | B2 | 12/2015 | Kim et al. |
| 9,259,291 | B2 | 2/2016 | Gantes |
| 9,504,579 | B2 | 11/2016 | Mahfouz et al. |
| 9,642,633 | B2 | 5/2017 | Frey et al. |
| 9,788,907 | B1 | 10/2017 | Alvi et al. |
| 9,814,533 | B2 | 11/2017 | Park et al. |
| 9,839,438 | B2 | 12/2017 | Eash |
| 9,861,446 | B2 | 1/2018 | Lang |
| 9,956,089 | B2 | 5/2018 | Kelman et al. |
| 9,987,024 | B2 | 6/2018 | Frey et al. |
| 10,019,551 | B2 | 7/2018 | Zellner et al. |
| 10,052,170 | B2 | 8/2018 | Saget et al. |
| 10,070,928 | B2 | 9/2018 | Frank et al. |
| 10,102,309 | B2 | 10/2018 | McKinnon et al. |
| 10,130,378 | B2 | 11/2018 | Bryan |
| 10,154,239 | B2 | 12/2018 | Casas |
| 10,159,513 | B2 | 12/2018 | Pavlovskaia et al. |
| 10,182,870 | B2 | 1/2019 | Park et al. |
| 10,194,990 | B2 | 2/2019 | Amanatullah et al. |
| 10,206,727 | B2 | 2/2019 | Ponce et al. |
| 10,262,084 | B2 | 4/2019 | Lavallee et al. |
| 10,368,947 | B2 | 8/2019 | Lang |
| 10,600,515 | B2 | 3/2020 | Otto et al. |
| 10,667,867 | B2 | 6/2020 | Gangwar et al. |
| 10,675,063 | B2 | 6/2020 | Pavlovskaia et al. |
| 10,722,310 | B2 | 7/2020 | Luby |
| 10,762,623 | B2 | 9/2020 | Geebelen et al. |
| 10,864,057 | B2 | 12/2020 | Chappuis et al. |
| 10,973,535 | B2 | 4/2021 | Tannotti et al. |
| 10,973,580 | B2 | 4/2021 | Berend et al. |
| 11,051,830 | B2 | 7/2021 | Jaramaz et al. |
| 11,071,592 | B2 | 7/2021 | McGuan et al. |
| 2002/0082498 | A1 | 6/2002 | Wendt et al. |
| 2006/0142657 | A1 | 6/2006 | Quaid et al. |
| 2007/0248261 | A1* | 10/2007 | Zhou ..................... G06T 19/006 382/154 |
| 2009/0069823 | A1 | 3/2009 | Foerster et al. |
| 2010/0234770 | A1 | 9/2010 | Colombet et al. |
| 2011/0257653 | A1 | 10/2011 | Hughes et al. |
| 2012/0209394 | A1 | 8/2012 | Bojarski et al. |
| 2014/0121715 | A1 | 5/2014 | May et al. |
| 2016/0256222 | A1 | 9/2016 | Walch |
| 2016/0324580 | A1 | 11/2016 | Esterberg |
| 2017/0000562 | A1 | 1/2017 | Frank et al. |
| 2017/0027702 | A1 | 2/2017 | Goldstein et al. |
| 2017/0189119 | A1 | 7/2017 | Yildirim et al. |
| 2017/0258526 | A1 | 9/2017 | Lang |
| 2017/0296205 | A1* | 10/2017 | Iannotti .............. A61B 17/1739 |
| 2017/0299864 | A1 | 10/2017 | Vallius et al. |
| 2018/0000547 | A1 | 1/2018 | Kang et al. |
| 2018/0008418 | A1 | 1/2018 | Bonutti |
| 2018/0049622 | A1 | 2/2018 | Ryan et al. |
| 2018/0052277 | A1 | 2/2018 | Schowengerdt et al. |
| 2018/0092699 | A1 | 4/2018 | Finley |
| 2018/0233222 | A1 | 8/2018 | Daley et al. |
| 2018/0235762 | A1 | 8/2018 | Radermacher et al. |
| 2018/0250138 | A1 | 9/2018 | Alidousti et al. |
| 2018/0253838 | A1 | 9/2018 | Sperling et al. |
| 2018/0256259 | A1 | 9/2018 | Crawford |
| 2018/0344308 | A1 | 12/2018 | Nawana et al. |
| 2019/0021800 | A1 | 1/2019 | Crawford et al. |
| 2019/0239973 | A9 | 8/2019 | Esterberg et al. |
| 2019/0254750 | A1 | 8/2019 | Metz |
| 2019/0380792 | A1 | 12/2019 | Poltaretskyi et al. |
| 2019/0388153 | A1 | 12/2019 | Running et al. |
| 2020/0030036 | A1 | 1/2020 | Forstein |
| 2020/0085511 | A1 | 3/2020 | Oezbek et al. |
| 2020/0229869 | A1 | 7/2020 | Dorman |
| 2021/0093389 | A1* | 4/2021 | Poltaretskyi ........... G16H 40/67 |
| 2021/0161613 | A1 | 6/2021 | Poltaretskyi et al. |
| 2022/0039868 | A1 | 2/2022 | Chaoui et al. |
| 2022/0047400 | A1 | 2/2022 | Chaoui et al. |
| 2022/0054195 | A1 | 2/2022 | Chaoui et al. |
| 2022/0059212 | A1 | 2/2022 | Chaoui et al. |
| 2022/0059213 | A1 | 2/2022 | Chaoui et al. |
| 2022/0125519 | A1* | 4/2022 | Slagmolen ............. A61B 90/36 |
| 2022/0156924 | A1 | 5/2022 | Poltaretskyi et al. |
| 2022/0160439 | A1 | 5/2022 | Ryan et al. |
| 2022/0183758 | A1 | 6/2022 | Bailey |
| 2022/0265355 | A1 | 8/2022 | Ferrante et al. |
| 2022/0361962 | A1 | 11/2022 | Finley et al. |

FOREIGN PATENT DOCUMENTS

| | | | |
|---|---|---|---|
| CN | 109330677 | A | 2/2019 |
| JP | 2014180490 | A | 9/2014 |
| JP | 2017176803 | A | 10/2017 |
| JP | 2017221273 | A | 12/2017 |
| JP | 2018000949 | A | 1/2018 |
| JP | 2018532454 | A | 11/2018 |
| WO | 2016102025 | A1 | 6/2016 |
| WO | 2017041080 | A1 | 3/2017 |
| WO | 2017066518 | A1 | 4/2017 |
| WO | 2018005907 | A1 | 1/2018 |
| WO | 2018067966 | A1 | 4/2018 |
| WO | 2018200767 | A1 | 11/2018 |
| WO | 2019014278 | A1 | 1/2019 |
| WO | 2019014281 | A1 | 1/2019 |
| WO | 2019033037 | A2 | 2/2019 |
| WO | 2019213777 | A1 | 11/2019 |
| WO | 2019245849 | A1 | 12/2019 |
| WO | 2019245857 | A1 | 12/2019 |
| WO | 2020123701 | A1 | 6/2020 |
| WO | 2020123702 | A1 | 6/2020 |
| WO | 2021007418 | A2 | 1/2021 |
| WO | 2021225840 | A1 | 11/2021 |
| WO | 2022136169 | A1 | 6/2022 |
| WO | 2023183644 | A1 | 9/2023 |

OTHER PUBLICATIONS

"Blueprint 3d Planning Software + PSI," Wright Medical Group, retrieved from https://www.wright.com/blueprint-3d-planning-psi-system on Oct. 15, 2020, 9 pp.

"Hololens 2," Microsoft Hololens, retrieved from https://www.microsoft.com/en-us/hololens, on Oct. 15, 2020, 5 pp.

Abdelhameed et al., "Neural network-based shoulder instability diagnosis modeling for robot-assisted rehabilitation systems", Sys-

(56) References Cited

OTHER PUBLICATIONS tems Science & Control Engineering, vol. 3, No. 1, 2015, pp. 514-523.
Birkfellner et al., "Chapter 2—Tracking Devices," from Image—Guided Interventions, Springer Science, 2008, 23 pp. (Applicant points out, in accordance with MPEP 609.04(a), that the year of publication, 2008, is sufficiently earlier than the effective U.S. filing date, so that the particular month of publication is not in issue.).
Boissonnat, J.D., "Shape Reconstruction from Planar Cross Sections," Computer Vision, Graphics, and Image Processing, vol. 44, No. 1, Oct. 1988, 29 pp.
Brochure entitled "Tornier SIMPLICITI™ Shoulder System," by Wright Medical Group, downloaded from https://www.wright.com/products-upper/simpliciti-shoulder-arthroplasty-system on May 1, 2020, 1 pp.
Brochure entitled "Tornier SIMPLICITI™ Shoulder System," by Wright Medical Group, downloaded from https://www.wright.com/products-upper/simpliciti-shoulder-arthroplasty-system on Nov. 2, 2021, 6 pp.
Brochure entitled "Tornier, SIMPLICITI™ Shoulder System—Surgical Technique (CAW-7656_EN_LR_LE)," by Wright Medical Group, downloaded from https://www.wrightemedia.com/ProductFiles/Files/PDFs/CAW-7656_EN_LR_LE.pdf on Nov. 2, 2021, dated Jan. 14, 2016, 24 pp.
Brochure entitled "Zimmer® PSI Shoulder for Trabecular Metal™ Reverse Glenoid," from Zimmer, #97-4309-040-00, Dec. 16, 2013, 6 pp.
Daftry et al., "Flexible and User-Centric Camera Calibration using Planar Fiducial Markers," British Machine Vision Conference, Sep. 9-13, 2013, 13 pp.
Franz et al., "Electromagnetic Tracking in Medicine—A Review of Technology, Validation, and Applications," IEEE Transactions on Medical Imaging, vol. 33, No. 8, Aug. 2014, pp. 1702-1725.
Giannotti et al., "Indices of risk assessment of fracture of the proximal humerus," Clinical cases in mineral and bone metabolism: the official journal of the Italian Society of Osteoporosis, Mineral Metabolism, and Skeletal Diseases, vol. 9, No. 1, Jan. 2012, 3 pp.
Gibby et al., "Head-mounted display augmented reality to guide pedicle screw placement utilizing computed tomography," International Journal of Computer Assisted Radiology and Surgery, vol. 14, No. 3, Jun. 2018, 11 pp.
International Preliminary Report on Patentability from International Application No. PCT/US2021/029572 dated Nov. 17, 2022, 9 pp.
International Search Report and Written Opinion of International Application No. PCT/US2021/029572, dated Aug. 10, 2021, 13 pp.
ITk::BSplineScatteredDataPointSetToImageFilter<TInputPointSet, TOutputImage> Class Template Reference, from ITK r.11.0 Insight Segmentation and Registration Toolkit. downloaded from https://itk.org/Doxygen411/html/classitk_1_1BSplineScatteredDataPointSetToImageFilter.html on Nov. 10, 2021, 24 pp.
Lee et al., "Multi-modal imaging, model-based tracking, and mixed reality visualisation for orthopaedic surgery," Healthcare Technology Letters, vol. 4, No. 5, Sep. 2017, 6 pp.
Lee et al., "Scattered Data Interpolation with Multilevel B-Splines," IEEE Transactions on Visualization and Computer Science, vol. 3, No. 3, Ju.-Sep. 1997, 17 pp.
Marker et al., "Contour-Based Surface Reconstruction using Implicit Curve Fitting, and Distance Field Filtering and Interpolation," Volume Graphics, Jan. 2006, 9 pp.
Mather et al., "Proximal humerus cortical bone thickness correlates with bone mineral density and can clinically rule but osteoporosis," Journal of Shoulder and Elbow Surgery, vol. 22, No. 6, Jun. 2013, 7 pp.
Nguyen et al., "A new segmentation method for MRI images of the shoulder joint," Fourth Canadian Conference on Computer and Robot Vision (CRV'07), May 2007, 8 pp.
Prophecy Infinity Pre-Operative navigation Guides—Surgical Technique, by Wright Medical Technology, Inc., Oct. 2014, 80 pp.
Tan et al., "6D Object Pose Estimation with Depth Images: A Seamless Approach for Robotic Interaction and Augmented Reality," Sep. 5, 2017, 4 pp.
Tingart et al., "The cortical thickness of the proximal humeral diaphysis predicts bone mineral density of the proximal humerus," The Journal of Bone & Joint Surgery, vol. 85-B, No. 4, May 2003, accepted after revision Sep. 24, 2002, 7 pp.
Tustison et al., "N-D Ck B-Spline Scattered Data Approximation," The Insight Journal, Aug.-Dec. 2005, 13 pp.
U.S. Appl. No. 17/413,414, filed Dec. 11, 2019, naming inventors Chaoui et al.
U.S. Appl. No. 17/413,432, filed Dec. 11, 2019, naming inventors Chaoui et al.
U.S. Appl. No. 17/413,444, filed Dec. 11, 2019, naming inventors Chaoui et al.
U.S. Appl. No. 17/413,453, filed Dec. 11, 2019, naming inventors Chaoui et al.
U.S. Appl. No. 17/413,460, filed Dec. 11, 2019, naming inventors Chaoui et al.
U.S. Appl. No. 17/435,978, filed Mar. 18, 2020, naming inventors Poltaretskyi et al.
Verborgt et al., "Accuracy of patient-specific guided implantation of the glenoid component in reversed shoulder arthroplasty," Orthopaedics & Traumatology: Surgery & Research, vol. 104, No. 6, Jan. 2018, 6 pp.
Wright Medical, "BluePrint Video-Wright Medical Announces the Acquisition of IMASCAP SAS", accessed from www.imascap.com/wp-content/uploads/2017/12/blueprintvid.mp4, Dec. 14, 2017, 9 pp.
Wright, "Aequalis Ascend Flex, Convertible Shoulder System," CAW-5396, Tornier, Mar. 2017, 88 pp.
Wright, "Aequalis Perform, Anatomic Glenoid System," CAW-5233, Tornier, Jul. 2017, 36 pp.
Wright, "Aequalis Reversed II Shoulder System," Tornier, CAW-2145, May 12, 2016, 52 pp.
Wright, "BluePrint, 3d Planning + PSI," User Manual V2.1, Tornier, CAW-8754, Nov. 2017, 18 pp.
First Examination Report from counterpart Australian Application No. 2021267483 dated Oct. 18, 2023, 4 pp.
Response to Communication under Rule 161/162 dated Dec. 13, 2022, from counterpart European Application No. 21730326.2 filed Jun. 7, 2023, 24 pp.
Office Action from counterpart Australian Application No. 2021267483 dated Mar. 26, 2024, 3 pp.
Response to Office Action dated Oct. 18, 2023, from counterpart Australian Application No. 2021267483 filed Feb. 28, 2024, 89 pp.
Response to Second Examination Report dated Mar. 26, 2024, from counterpart Australian Application No. 2021267483 filed May 22, 2024, 84 pp.
Third Examination Report from counterpart Australian Application No. 2021267483 dated Jun. 18, 2024, 5 pp.
Wikipedia page for Quadratic, published on May 3, 2020 as per Wayback Machine URL: https://web.archive.org/web/20200503024138/https://en.wikipedia.org/wiki/Quadric.
Wikipedia page for Paraboloid, published on Feb. 13, 2020 as per Wayback Machine URL: https://web.archive.org/web/20200213015844/https://en.wikipedia.org/wiki/Paraboloid.
Response to Third Examination Report dated Jun. 18, 2024, from counterpart Australian Application No. 2021267483 filed Sep. 3, 2024, 47 pp.
Notice of Intent to Grant from counterpart Australian Application No. 2021267483 dated Sep. 25, 2024, 3 pp.
Communication pursuant to Article 94(3) EPC from counterpart European Application No. 21730326.2 dated Feb. 28, 2025, 6 pp.
Response to Communication pursuant to Article 94(3) EPC dated Feb. 28, 2025, from counterpart European Application No. 21730326.2 filed Jun. 26, 2025, 17 pp.

* cited by examiner

MIXED REALITY-BASED SCREW TRAJECTORY GUIDANCE

This application is a national stage application under 35 U.S.C. § 371 of PCT Application No. PCT/US2021/029572, filed Apr. 28, 2021, which claims the benefit of U.S. Provisional Application No. 63/019,906, filed May 4, 2020, the entire content of both of which are incorporated herein by reference.

BACKGROUND

Many types of surgical procedures involve inserting screws into bones of a patient. For example, a surgical procedure may include using a set of screws to attach an orthopedic prosthesis to a bone. Proper insertion of screws may be a significant factor in the success of a surgical procedure. For instance, inserting a screw at an incorrect angle may lead to surgical complications.

SUMMARY

This disclosure describes a variety of techniques for providing mixed reality (MR)-based surgical guidance, such as MR-based screw trajectory guidance. The techniques described in this disclosure may be used independently or in various combinations.

In one example, this disclosure describes a method comprising: determining, by a surgical assistance system, a potential insertion point on a surface of a bone of a patient; and presenting, by a Mixed Reality (MR) visualization device of the surgical assistance system, an MR scene that includes a virtual trajectory guide, wherein: the virtual trajectory guide comprises an elliptical surface, and for each location of a plurality of locations on the elliptical surface: the location corresponds to a potential insertion axis that passes through the location and the potential insertion point on the surface of the bone, and the location is visually distinguished based on a quality of a portion of the bone along the potential insertion axis corresponding to the location.

In another example, this disclosure describes a method comprising: generating, by a surgical assistance system, a virtual bone quality map, wherein for each respective location in a plurality of locations on the virtual bone quality map: the respective location indicates a bone quality of a bone along a potential insertion axis corresponding to the respective location, and the potential insertion axis corresponding to the respective location passes through the bone and the respective location; and presenting, by a Mixed Reality (MR) visualization device of the surgical assistance system, an MR scene that includes the virtual bone quality map superimposed on a bone of the patient or a virtual model of the bone of the patient.

In another example, this disclosure describes a method comprising: presenting, by a MR visualization device of a surgical assistance system, an MR scene that includes a virtual insertion axis object aligned along a first axis that intersects a potential insertion point on a bone of a patient and has a first orientation; receiving, by the surgical assistance system, an indication of user input to change an orientation of the virtual insertion axis object relative to a surface of the bone from the first orientation to the second orientation; and in response to receiving the indication of user input: updating, by the MR visualization device, a position of the virtual insertion axis object so that the virtual insertion axis object is aligned along a second axis that intersects the potential insertion point on the bone and has the second orientation; and providing, by the surgical assistance system, user feedback with respect to a bone quality of the bone along the second axis.

The details of various examples of the disclosure are set forth in the accompanying drawings and the description below. Various features, objects, and advantages will be apparent from the description, drawings, and claims.

DETAILED DESCRIPTION

Figure 1:
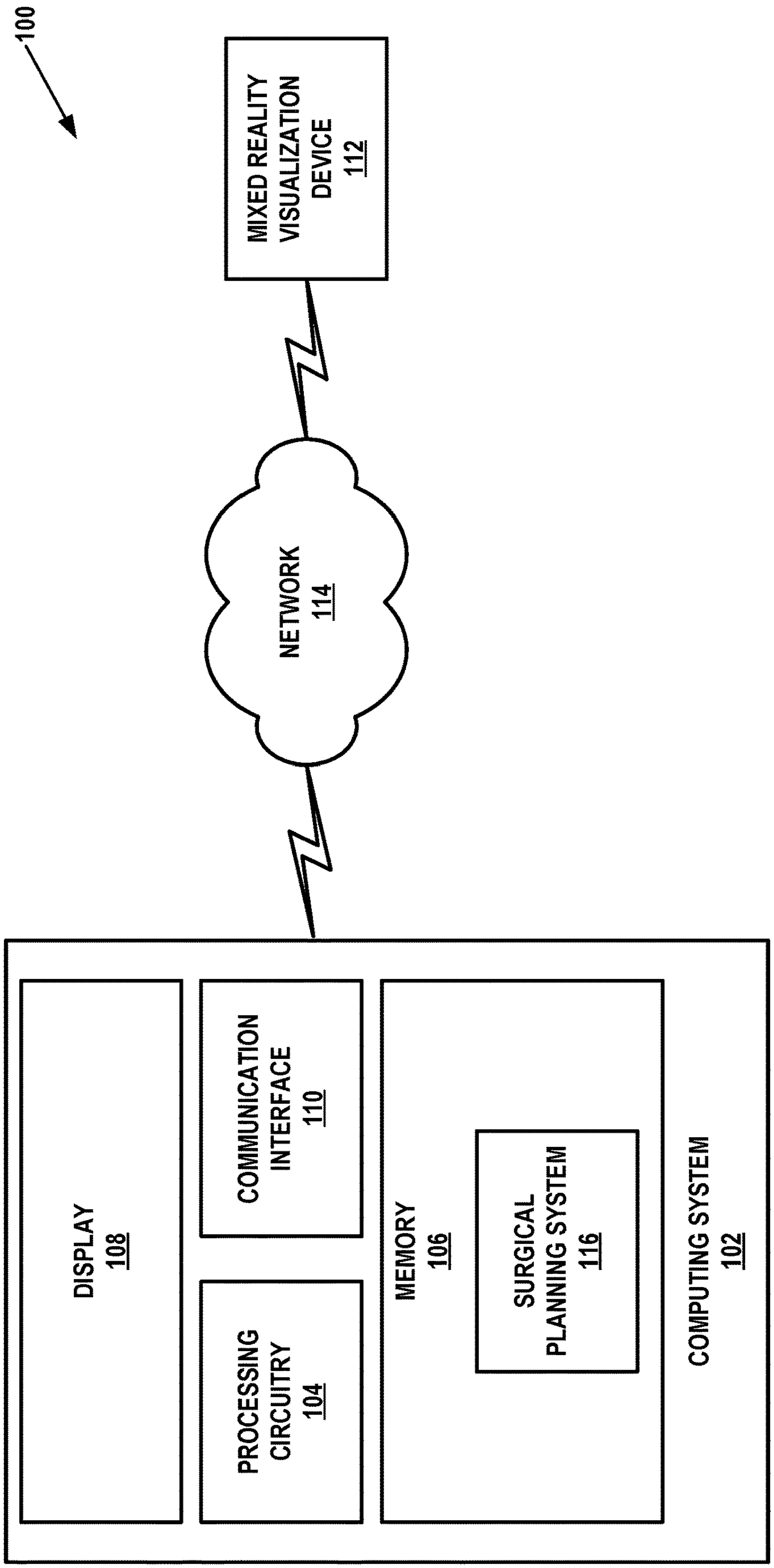
FIG. 1 is a block diagram of a surgical assistance system according to an example of this disclosure.

Certain examples of this disclosure are described with reference to the accompanying drawings, wherein like reference numerals denote like elements. It should be understood, however, that the accompanying drawings illustrate only the various implementations described herein and are not meant to limit the scope of various technologies described herein. The drawings show and describe various examples of this disclosure. In the following description, numerous details are set forth. However, it will be understood by those skilled in the art that the present invention may be practiced without these details and that numerous variations or modifications from the described examples may be possible.

This disclosure describes systems and methods associated with using mixed reality (MR) to assist with the planning and performance of a surgical procedure. A surgical plan, e.g., a surgical plan generated by the BLUEPRINT™ system produced by Wright Medical NV or another surgical planning platform, may include a variety of information regarding a surgical procedure. For example, a surgical plan may include information regarding steps to be performed on a patient by a user, such as a surgeon. Example steps may include, for example, bone or tissue preparation steps and/or steps for selection, modification and/or placement of implant components. Furthermore, information in a surgical plan may include, in various examples, dimensions, shapes, angles, surface contours, and/or orientations of implant components to be selected or modified by users, dimensions, shapes, angles, surface contours and/or orientations to be defined in bone or tissue by the user in bone or tissue preparation steps, and/or positions, axes, planes, angle and/or entry points defining placement of implant components by the user relative to patient bone or tissue. Information such as dimensions, shapes, angles, surface contours, and/or orientations of anatomical features of the patient may be derived from imaging (e.g., x-ray, CT, MRI, ultrasound or other images), direct observation, or other techniques.

In this disclosure, the term "mixed reality" (MR) refers to the presentation of virtual objects such that a user sees images that include both real, physical objects and virtual objects. Virtual objects may include text, 2-dimensional surfaces, 3-dimensional models, or other user-perceptible elements that are not actually present in the physical, real-world environment in which the virtual objects are presented as coexisting. In addition, virtual objects described in various examples of this disclosure may include graphics, images, animations or videos, e.g., presented as 3D virtual objects or 2D virtual objects. Virtual objects may also be referred to as virtual elements. Such virtual elements may or may not be analogs of real-world objects. In some examples, in mixed reality, a camera may capture images of the real world and modify the images to present virtual objects in the context of the real world. In such examples, the modified images may be displayed on a screen, which may be head-mounted, handheld, or otherwise viewable by a user. This type of mixed reality is increasingly common on smartphones, such as where a user can point a smartphone's camera at a sign written in a foreign language and see in the smartphone's screen a translation in the user's own language of the sign superimposed on the sign along with the rest of the scene captured by the camera. In some examples, in mixed reality, see-through (e.g., transparent) holographic lenses, which may be referred to as waveguides, may permit the user to view real-world objects, i.e., actual objects in a real-world environment, such as real anatomy, through the holographic lenses and also concurrently view virtual objects. In this disclosure, the term "MR scene" may apply to a scene, as perceived by a user, that includes one or more virtual objects.

The Microsoft HOLOLENS™ headset, available from Microsoft Corporation of Redmond, Washington, is an example of an MR device that includes see-through holographic lenses that permit a user to view real-world objects through the lens and concurrently view projected 3D holographic objects. The Microsoft HOLOLENS™ headset, and similar waveguide-based visualization devices, are examples of MR visualization devices that may be used in accordance with some examples of this disclosure. Some holographic lenses may present holographic objects with some degree of transparency through see-through holographic lenses so that the user views real-world objects and virtual, holographic objects. In some examples, some holographic lenses may, at times, completely prevent the user from viewing real-world objects and instead may allow the user to view entirely virtual environments. The term mixed reality may also encompass scenarios where one or more users are able to perceive one or more virtual objects generated by holographic projection. In other words, "mixed reality" may encompass the case where a holographic projector generates holograms of elements that appear to a user to be present in the user's actual physical environment.

In some examples, in mixed reality, the positions of some or all presented virtual objects are related to positions of physical objects in the real world. For example, a virtual object may be tethered to a table in the real world, such that the user can see the virtual object when the user looks in the direction of the table but does not see the virtual object when the table is not in the user's field of view. In some examples, in mixed reality, the positions of some or all presented virtual objects are unrelated to positions of physical objects in the real world. For instance, a virtual item may always appear in the top right of the user's field of vision, regardless of where the user is looking.

Augmented reality (AR) is similar to MR in the presentation of both real-world and virtual elements, but AR generally refers to presentations that are mostly real, with a few virtual additions to "augment" the real-world presentation. For purposes of this disclosure, MR is considered to include AR. For example, in AR, parts of the user's physical environment that are in shadow can be selectively brightened without brightening other areas of the user's physical environment. This example is also an instance of MR in that the selectively brightened areas may be considered virtual objects superimposed on the parts of the user's physical environment that are in shadow.

FIG. 1 is a block diagram illustrating an example surgical assistance system 100 that may be used to implement the techniques of this disclosure. FIG. 1 illustrates computing system 102, which is an example of a computing system configured to perform one or more example techniques described in this disclosure. Computing system 102 may include various types of computing devices, such as server computers, personal computers, smartphones, wearable devices, laptop computers, and other types of computing devices. Computing system 102 includes processing circuitry 104, memory 106, a display 108, and a communication interface 110. Display 108 may be optional, such as in examples where computing system 102 comprises a server computer.

Examples of processing circuitry 104 include one or more microprocessors, digital signal processors (DSPs), application specific integrated circuits (ASICs), field programmable gate arrays (FPGAs), hardware, or any combinations thereof. In general, processing circuitry 104 may be implemented as fixed-function circuits, programmable circuits, or a combination thereof. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits.

Processing circuitry 104 may include arithmetic logic units (ALUs), elementary function units (EFUs), digital circuits, analog circuits, and/or programmable cores, formed from programmable circuits. In examples where the operations of processing circuitry 104 are performed using software executed by the programmable circuits, memory 106 may store the object code of the software that processing circuitry 104 receives and executes, or another memory within processing circuitry 104 (not shown) may store such instructions. Examples of the software include software designed for surgical planning. Processing circuitry 104 may perform the actions ascribed in this disclosure to computing system 102.

Memory 106 may store various types of data used by processing circuitry 104. For example, memory 106 may store data describing 3D models of various anatomical structures, including morbid and predicted premorbid anatomical structures. For instance, in one specific example, memory 106 may store data describing a 3D model of a predicted premorbid humerus of a patient.

Memory 106 may be formed by any of a variety of memory devices and/or storage devices, such as dynamic random access memory (DRAM), including synchronous DRAM (SDRAM), magnetoresistive RAM (MRAM), resistive RAM (RRAM), hard disk drives, optical discs, or other types of non-transitory computer-readable media. Examples of display 108 may include a liquid crystal display (LCD), a plasma display, an organic light emitting diode (OLED) display, or another type of display device.

Communication interface 110 allows computing system 102 to output data and instructions to and receive data and instructions from a MR visualization device 112 and/or other devices via a network 114. Communication interface 110 may comprise hardware circuitry that enables computing system 102 to communicate (e.g., wirelessly or using wires) to other computing systems and devices, such as MR visualization device 112. Network 114 may include various types of communication networks including one or more wide-area networks, such as the Internet, local area networks, and so on. In some examples, network 114 may include wired and/or wireless communication links.

MR visualization device 112 may use various visualization techniques to display image content to a user, such as a surgeon. MR visualization device 112 may be a mixed reality (MR) visualization device, holographic projector, or other device for presenting MR scenes. In some examples, MR visualization device 112 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Furthermore, in the example of FIG. 1, memory 106 may include computer-readable instructions that, when executed by processing circuitry 104, cause computing system 102 to provide a surgical planning system 116. In some examples, some or all of the instructions of surgical planning system 116 are stored on MR visualization device 112 and/or executed by processing circuitry of MR visualization device 112. As such, in some examples, the functionality described by the instructions of surgical planning system 116 may be distributed across computing system 102 and MR visualization device 112. For ease of explanation, this disclosure may simply describe actions performed by computing system 102 and/or MR visualization device 112 when processing circuitry 104 and/or processing circuitry of MR visualization device 112 executes instructions of surgical planning system 116 as being performed by surgical planning system 116.

One or more users may use surgical planning system 116 in a preoperative phase. For instance, surgical planning system 116 may help the one or more users generate a virtual surgical plan that may be customized to an anatomy of interest of a patient. The virtual surgical plan may include a 3-dimensional virtual model that corresponds to the anatomy of interest of the patient, 3-dimensional models of one or more prosthetic components matched to the patient to repair the anatomy of interest or selected to repair the anatomy of interest, and/or other information. The virtual surgical plan also may include a 3-dimensional virtual model of guidance information to guide a user in performing the surgical procedure, e.g., in preparing bone surfaces or tissue and placing implantable prosthetic hardware relative to such bone surfaces or tissue. In accordance with one or more techniques of this disclosure, the virtual surgical plan may also include information regarding trajectories for inserting screws, pins, or other items into a bone of the patient.

Surgical planning system 116 may be configured to cause display 108 and/or MR visualization device 112 to display virtual guidance including one or more virtual guides for performing work on a portion of a patient's anatomy. For instance, surgical planning system 116 may cause display 108 to display virtual guidance, such as 3-dimensional virtual models of bones and other virtual objects, on display 108 during a preoperative planning phase of a surgical procedure. Surgical planning system 116 may cause MR visualization device 112 to present an MR scene that includes virtual guidance during an intraoperative phase (i.e., during performance of) the surgical procedure.

When surgical planning system 116 causes MR visualization device 112 to present an MR scene, a user of MR visualization device 112 may be able to view real-world objects along with virtual objects. For instance, the user of MR visualization device 112 may be able to see objects in a real-world environment, such as a surgical operating room. In this disclosure, the terms real and real-world may be used in a similar manner. The real-world objects viewed by the user in the real-world scene may include the patient's actual, real anatomy, such as an actual glenoid or humerus, exposed during a surgical procedure.

MR visualization device 112 may be a head-mounted MR visualization device and the user of MR visualization device 112 may view real-world objects via a see-through (e.g., transparent) screen, such as see-through holographic lenses, of MR visualization device 112 and also see virtual guidance that appear to be projected on the screen or within the real-world scene, such that the MR guidance object(s) appear to be part of the real-world scene, e.g., with the virtual objects appearing to the user to be integrated with the actual, real-world scene. For example, the virtual guidance may be projected on the screen of a MR visualization device 112, such that the virtual guidance is overlaid on, and appears to be placed within, an actual, observed view of the patient's actual bone viewed by the user through the transparent screen, e.g., through see-through holographic lenses. Hence, in this example, the virtual guidance may be a virtual 3D object that appears to be part of the real-world environment, along with actual, real-world objects.

Certain techniques of this disclosure are described below with respect to a shoulder arthroplasty surgical procedure and particularly with respect to a human scapula. Examples of shoulder arthroplasties include, but are not limited to, reversed arthroplasty, augmented reverse arthroplasty, standard total shoulder arthroplasty, augmented total shoulder arthroplasty, and hemiarthroplasty. However, the techniques are not so limited, and the visualization system may be used to provide virtual guidance information, including virtual guides in any type of surgical procedure. Other example procedures in which surgical assistance system 100 may be used to provide virtual guidance include, but are not limited to, other types of orthopedic surgeries; any type of procedure with the suffix "plasty," "stomy," "ectomy," "clasia," or "centesis,"; orthopedic surgeries for other joints, such as elbow, wrist, finger, hip, knee, ankle or toe, or any other orthopedic surgical procedure in which precision guidance is desirable. For instance, surgical assistance system 100 may be used to provide virtual guidance for an ankle arthroplasty surgical procedure.

As described herein, surgical assistance system 100 may provide virtual guidance that may help a user, such as a surgeon, insert screws, pins, or other objects into a bone of a patient at an appropriate angle. For instance, in accordance with some examples, MR visualization device 112 may present an MR scene that includes a virtual trajectory guide. In this example, the virtual trajectory guide comprises an elliptical surface and, for each location of a plurality of locations on the elliptical surface, the location corresponds to a potential insertion axis that passes through the location and the potential insertion point on the surface of the bone. In this example, the location may be visually distinguished (e.g., color-coded) based on a quality of a portion of the bone along the potential insertion axis corresponding to the location.

Furthermore, in accordance with some examples of this disclosure, MR visualization device 112 may present an MR scene that includes a virtual bone quality map superimposed on a bone of the patient or a virtual model of the bone of the patient. In such examples, for each respective location in a plurality of locations on the virtual bone quality map, the respective location indicates a bone quality of the bone along a potential insertion axis corresponding to the respective location. In such examples, the potential insertion axis corresponding to the respective location passes through the bone and the respective location.

In accordance with some examples of this disclosure, MR visualization device 112 may present an MR scene that includes a virtual insertion axis object aligned along a first axis that intersects a potential insertion point on a bone of the patient or a virtual model of the bone of the patient and has a first orientation. Additionally, surgical assistance system 100 may receive an indication of user input to change an orientation of the virtual insertion axis object relative to a surface of the bone or virtual model of the bone from the first orientation to the second orientation. In response to receiving the indication of user input, MR visualization device 112 may update a position of the virtual insertion axis object so that the virtual insertion axis object is aligned along a second axis that intersects the potential insertion point and has the second orientation. Furthermore, in response to receiving the indication of user input, surgical assistance system 100 may provide user feedback with respect to a bone quality of the bone along the second axis.

Figure 2:
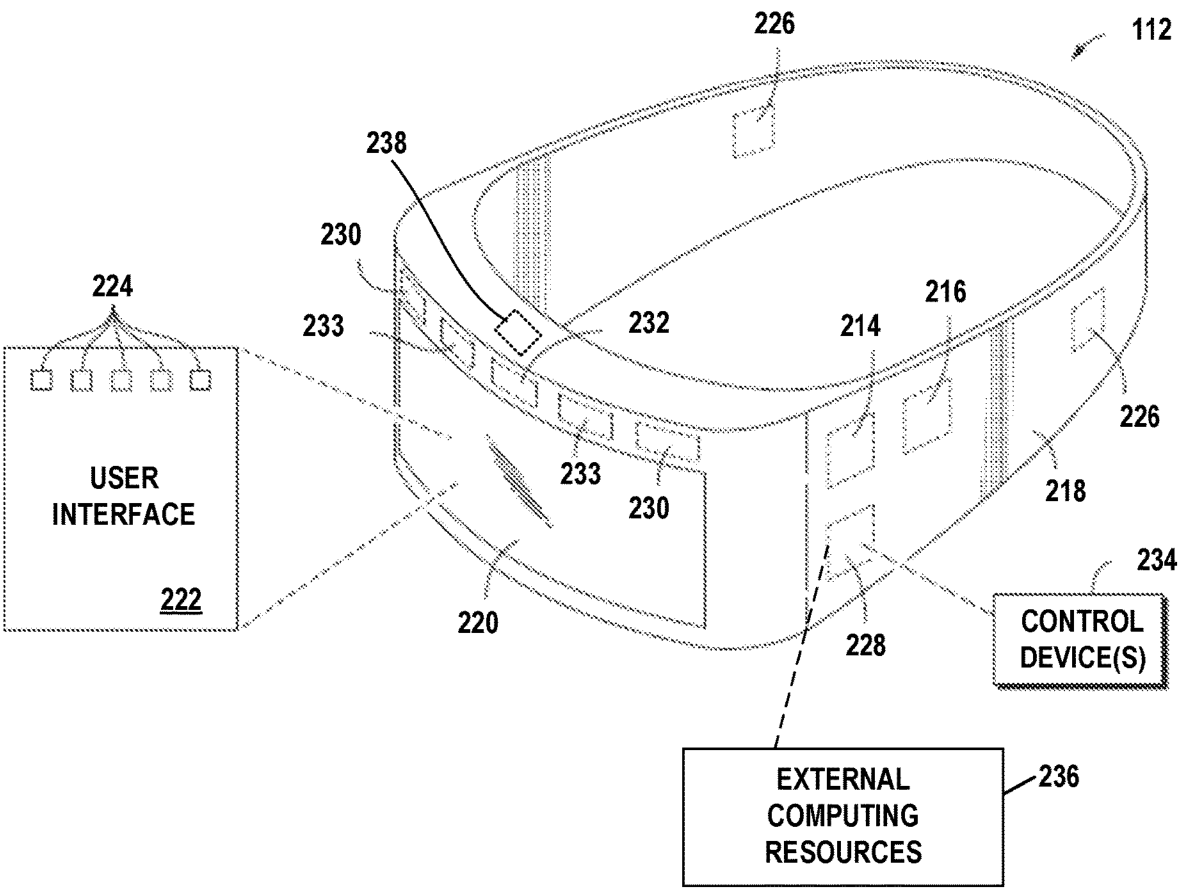
FIG. 2 is a schematic representation of a Mixed Reality (MR) visualization device for use in the surgical assistance system of FIG. 1, according to an example of this disclosure.

FIG. 2 is a schematic representation of MR visualization device 112 for use in surgical assistance system 100 of FIG. 1, according to an example of this disclosure. As shown in the example of FIG. 2, MR visualization device 112 can include a variety of electronic components found in a computing system, including one or more processor(s) 214 (e.g., microprocessors or other types of processing units) and memory 216 that may be mounted on or within a frame 218. Although the example of FIG. 2 illustrates MR visualization device 112 as a head-wearable device, MR visualization device 112 may have other forms and form factors. For instance, in some examples, MR visualization device 112 may be a handheld smartphone or tablet.

In the example of FIG. 2, MR visualization device 112 includes a transparent screen 220 that is positioned at eye level when MR visualization device 112 is worn by a user. In some examples, screen 220 may include one or more liquid crystal displays (LCDs), organic light emitting diode (OLED) displays, or other types of display screens on which images are perceptible to a user who is wearing or otherwise using MR visualization device 112. In some examples, MR visualization device 112 can operate to project 3D images onto the user's retinas using techniques known in the art.

In some examples, screen 220 may include see-through holographic lenses, which are sometimes referred to as waveguides. The see-through holographic lenses permit a user to see real-world objects through (e.g., beyond) the see-through holographic lenses and also see holographic imagery projected into the see-through holographic lenses and from there onto the user's retinas. The holographic imagery may be projected by displays, such as liquid crystal on silicon (LCoS) display devices, which are sometimes referred to as light engines or projectors, operating as a holographic projection system 238 within MR visualization device 112. Hence, in some examples, MR visualization device 112 can project 3D images onto the user's retinas via screen 220. In this manner, MR visualization device 112 may be configured to present a virtual image to a user within a real-world view observed through screen 220, e.g., such that the virtual image appears to form part of the real-world environment. In some examples, MR visualization device 112 may be a Microsoft HOLOLENS™ headset, available from Microsoft Corporation, of Redmond, Washington, USA, or a similar device, such as, for example, a similar MR visualization device that includes waveguides.

Furthermore, in the example of FIG. 2, MR visualization device 112 may generate a user interface (UI) 222 that is visible to the user, e.g., as holographic imagery projected into see-through holographic lenses as described above. UI 222 may include a variety of selectable widgets 224 that allow the user to interact with surgical planning system 116.

MR visualization device 112 also may include other components. For example, MR visualization device 112 may include one or more speakers or other sensory devices 226 that may be positioned adjacent the user's ears. Sensory devices 226 may convey audible information or other perceptible information (e.g., vibrations) to assist the user of MR visualization device 112. MR visualization device 112 can also include a transceiver 228 to connect MR visualization device 112 to network 114, such as via a wired or wireless communication channel.

MR visualization device 112 may also include a variety of sensors to collect sensor data, such as one or more optical camera(s) 230 (or other optical sensors) and one or more depth camera(s) 232 (or other depth sensors), mounted to, on or within frame 218. In some examples, the optical sensor(s) 230 are operable to scan the geometry of the physical environment in which user of computing system 102 is located (e.g., an operating room) and collect two-dimensional (2D) optical image data (either monochrome or color). Depth sensor(s) 232 are operable to provide 3D image data, such as by employing time of flight, stereo or other known or future-developed techniques for determining depth and thereby generating image data in three dimensions. Other sensors of MR visualization device 112 may include motion sensors 233 (e.g., Inertial Measurement Unit (IMU) sensors, accelerometers, gyroscopes, etc.) to assist with tracking movement.

Surgical planning system 116 (FIG. 1) may process sensor data so that surgical planning system 116 may define geometric, environmental, textural, etc. landmarks (e.g., corners, edges or other lines, walls, floors, objects) in the user's environment and detect movements within the user's environment. As an example, surgical planning system 116 may combine or fuse various types of sensor data so that the user of MR visualization device 112 is able to perceive virtual objects that can be positioned or fixed and/or moved within an MR scene. When a virtual object is fixed in the MR scene, the user can walk around the virtual object, view the virtual object from different perspectives, and manipulate the virtual object within the scene using hand gestures, voice commands, gaze line (or direction) and/or other control inputs. As another example, surgical planning system 116 may process the sensor data so that the user can position a virtual object (e.g., a 3-dimensional bone model) on an observed physical object in the user's environment (e.g., a surface, the patient's real bone, etc.) and/or orient the virtual object with other virtual objects presented in the MR scene. In some examples, surgical planning system 116 may process the sensor data so that the user can position and fix virtual objects representing aspects of a surgical plan onto one or more surfaces, such as one or more walls of an operating room. Furthermore, in some examples, surgical planning system 116 may use the sensor data to recognize surgical instruments and the positions and/or locations of those surgical instruments.

MR visualization device 112 may include one or more processors 214 and memory 216, e.g., within frame 218 of MR visualization device 112. In some examples, one or more external computing resources 236 process and store information, such as sensor data, instead of or in addition to processor(s) 214 of MR visualization device 112 and memory 216 of MR visualization device 112. Computing system 102 may include external computing resources 236. For instance, external computing resources 236 may include processing circuitry 104 (FIG. 1) and/or memory 106 (FIG. 1) of computing system 102. In this way, processor(s) 214 and memory 216 of MR visualization device 112 may perform data processing and storage and/or some of the processing and storage requirements may be offloaded from MR visualization device 112. Hence, in some examples, operation of MR visualization device 112 may, in some examples, be controlled in part by a combination one or more processors 214 within MR visualization device 112 and processing circuitry 104 external to MR visualization device 112. In some examples, processor(s) 214 and memory 216 of MR visualization device 112 may provide sufficient computing resources to process the sensor data collected by cameras 230, 232 and motion sensors 233.

In some examples, surgical planning system 116 may process the sensor data using a Simultaneous Localization and Mapping (SLAM) algorithm, or other algorithm for processing and mapping 2D and 3D image data and tracking the position of MR visualization device 112 in the 3D scene. In some examples, image tracking may be performed using sensor processing and tracking functionality provided by the Microsoft HOLOLENS™ system, e.g., by one or more sensors and processors 214 within a MR visualization device 112 substantially conforming to the Microsoft HOLOLENS™ device or a similar MR visualization device.

In some examples, computing system 102 can also include user-operated control device(s) 234 that allow the user to operate computing system 102 and/or MR visualization device 112. As examples, control device(s) 234 may include a microphone, a touch pad, a control panel, a motion sensor or other types of control input devices with which the user can interact.

Many types of surgical procedures involve inserting a screw or pin into a bone of a patient. For example, many types of joint replacement surgeries involve the use of screws to attach an orthopedic prosthesis to a bone of a patient. For instance, in a total shoulder replacement procedure, a user attaches a glenoid implant to a glenoid fossa of a patient's scapula. In a trauma repair surgery, a user may attach a plate to connect two or more fragments of a bone.

In order to ensure stability of an orthopedic prosthesis, the screws should be inserted into high quality bone. In general, higher quality bone is associated with higher density of the bone. In some examples, higher quality bone may be associated with greater density of bone (e.g., in terms of Hounsfield units) in Digital Imaging and Communications in Medicine (DICOM) images. Insertion of the screws into low quality bone may lead to fractures of the bone and loosening or failure of the orthopedic prosthesis. Therefore, it may be important that the screws be inserted through the orthopedic prosthesis into the highest quality bone available.

To attach an orthopedic prosthesis to a bone, a user may first drill a hole into the bone (e.g., a pilot hole) at an entry point corresponding to a screw hole defined by the orthopedic prosthesis. After drilling the hole in the bone, the user may pass a screw through the screw hole defined by the orthopedic prosthesis and into the hole drilled into the bone. The user may then use a screwdriver to tighten the screw, thereby securing the orthopedic prosthesis to the bone. In some examples, rather than using a drill to insert a screw into the bone, the user may instead use a self-tapping screw that passes through a screw hole defined by the orthopedic prosthesis into the bone.

Customized orthopedic prostheses can be manufactured with patient-specific screw holes that are aligned with areas of good bone quality. However, manufacturing such a customized orthopedic prosthesis may add to the cost of the surgical procedure and delay performance of the surgical procedure. Therefore, it may be desirable to instead use a limited range of orthopedic prostheses that are not patient-specific. However, this may lead to situations in which one or more screw holes defined in the orthopedic prostheses are not aligned with areas of good bone quality.

In some types of orthopedic prostheses, a user can pass a screw through a screw hole of an orthopedic prosthesis at an angle that is not orthogonal to the surface of the bone. For instance, the screw hole may allow for a screw to be inserted through the screw hole at an angle of up to a given number of degrees (e.g., 20°) relative to a line passing orthogonally through the screw hole. In other words, the screw can be tilted at a variety of angles within the screw hole without significantly diminishing the value of the screw in attaching the orthopedic prosthesis to the bone.

A user may take advantage of the ability to tilt a screw within a screw hole in order to ensure that the screw enters an area of good bone quality. For instance, if the user were to tilt a screw 15° posteriorly through a screw hole of an orthopedic prosthesis, the screw may enter an area of good bone quality; while if the user were to tilt the screw 15° anteriorly through the same screw hole, the screw may only enter areas of poor bone quality.

Similar considerations with respect to bone quality and angling may apply with respect to surgical pins that may be temporarily or permanently inserted into a bone of a patient. However, for ease of explanation, many examples of this disclosure are described with respect to screws. Such examples may also apply with respect to surgical pins or other types of items that may be inserted into a bone of a patient.

Figure 3A:
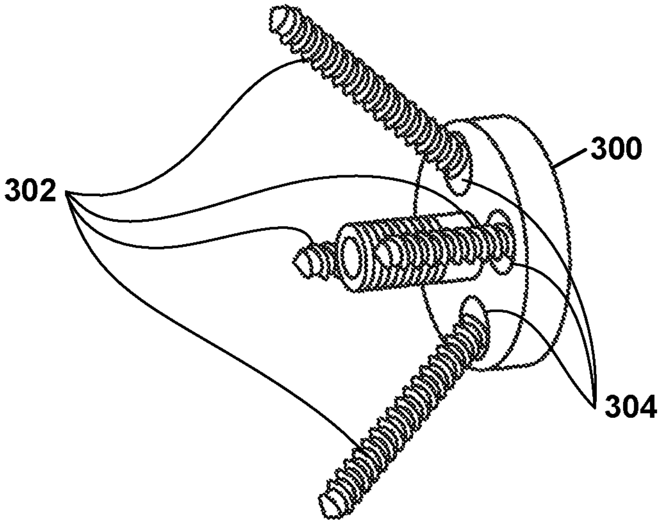
FIG. 3A is a conceptual diagram illustrating an example orthopedic prosthesis with screws extending through screw holes defined in the orthopedic prosthesis.
Figure 3B:
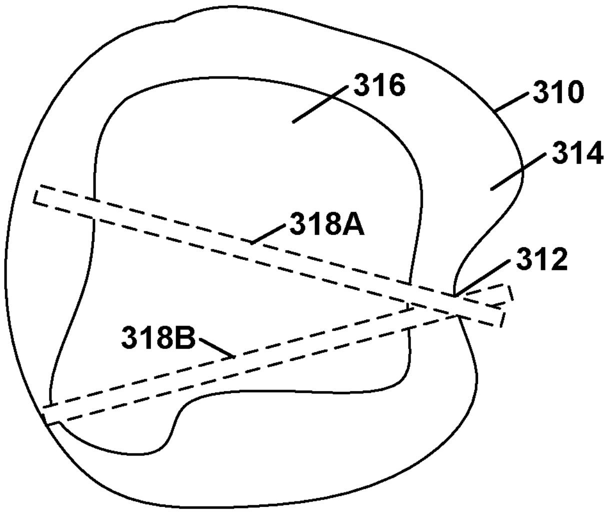
FIG. 3B is a conceptual diagram illustrating an example cross-section of a bone.

FIG. 3A is a conceptual diagram illustrating an example orthopedic prosthesis 300 with screws 302 extending through screw holes 304 defined in orthopedic prosthesis 300. FIG. 3B is a conceptual diagram illustrating an example cross-section of a bone 310. As shown in the example of FIG. 3B, a screw may be inserted into bone 310 through an insertion point 312. Area 314 of bone 310 represents cortical bone and area 316 of bone 310 represents cancellous bone. In general, cancellous bone is not associated with good bone quality because cancellous bone may not have sufficient density to ensure that a screw will stay in position. In contrast, cortical bone has greater density (e.g., than cancellous bone) and accordingly may be associated with higher bone quality. Osteophytes and abscesses are also associated with poor bone quality. However, as shown in the example of FIG. 3B, the cortical bone may not be a consistent thickness around a perimeter of a bone.

A screw may be inserted into bone 310 at different angles, as represented by dashed rectangles 318A and 318B. As shown in the example of FIG. 3B, when the screw is inserted into bone 310 according to the angle represented by dashed rectangle 318A, the screw may encounter more cortical bone than when the screw is inserted into bone 310 according to the angle represented by dashed rectangle 318B. Thus, it may be preferable to insert the screw according to the angle represented by dashed rectangle 318A as opposed to the angle represented by dashed rectangle 318B.

Similar considerations apply with respect to drilling holes for the insertion of surgical pins. Surgical pins may be used as guides or supports during surgical procedures. For example, a surgical pin may be used to temporarily attach a cutting jig to a bone, such as a humerus, to guide removal of a part of the bone. The user may insert the surgical pin through a corresponding hole of the cutting jig at different angles in order to ensure that the surgical pin enters an area of good bone quality.

This disclosure describes example MR-based techniques that may help a user insert a surgical item into a bone along a trajectory through the bone so that the surgical item encounters areas of good bone quality. For instance, with respect to the example of FIG. 3B, surgical assistance system 100 may help the user insert a screw or other surgical item into bone 310 according to the angle represented by dashed rectangle 318A as opposed to the angle represented by dashed rectangle 318B. The examples of this disclosure may be used separately or in combination. In instances where examples of this disclosure are used in combination, the examples may be used concurrently or at different times.

In some examples, surgical assistance system 100 may automatically determine an insertion angle of a screw or other surgical item for insertion point 312. For example, surgical assistance system 100 may generate a virtual model of a bone, e.g., based on patient-specific CT image data. Furthermore, surgical assistance system 100 may search through a set of available insertion angles to determine an insertion axis corresponding to a best bone quality value. The available insertion angles may be insertion angles through which the screw or other surgical item may be passed through an opening of a surgical prosthesis at insertion point. Surgical assistance system 100 may determine the bone quality value for the location as a sum of Hounsfield unit values of the voxels intersected by the potential insertion axis. In another instance, surgical planning system 116 may determine the bone quality value for the location as a sum of Hounsfield unit values of values intersected by the potential insertion axis that are above a specific threshold (e.g., so as to exclude voxels corresponding to cancellous bone). Surgical assistance system 100 may also determine a recommended length for the screw or other surgical item. Examples of determining the recommended length are provided elsewhere in this disclosure. Furthermore, surgical assistance system 100 may present the determined insertion axis and/or recommended length in a user interface, such as an MR scene. For instance, surgical assistance system 100 may present the determined insertion axis superimposed on the bone or a virtual model of the bone and/or may present the recommended length in a virtual element.

Figure 4A:
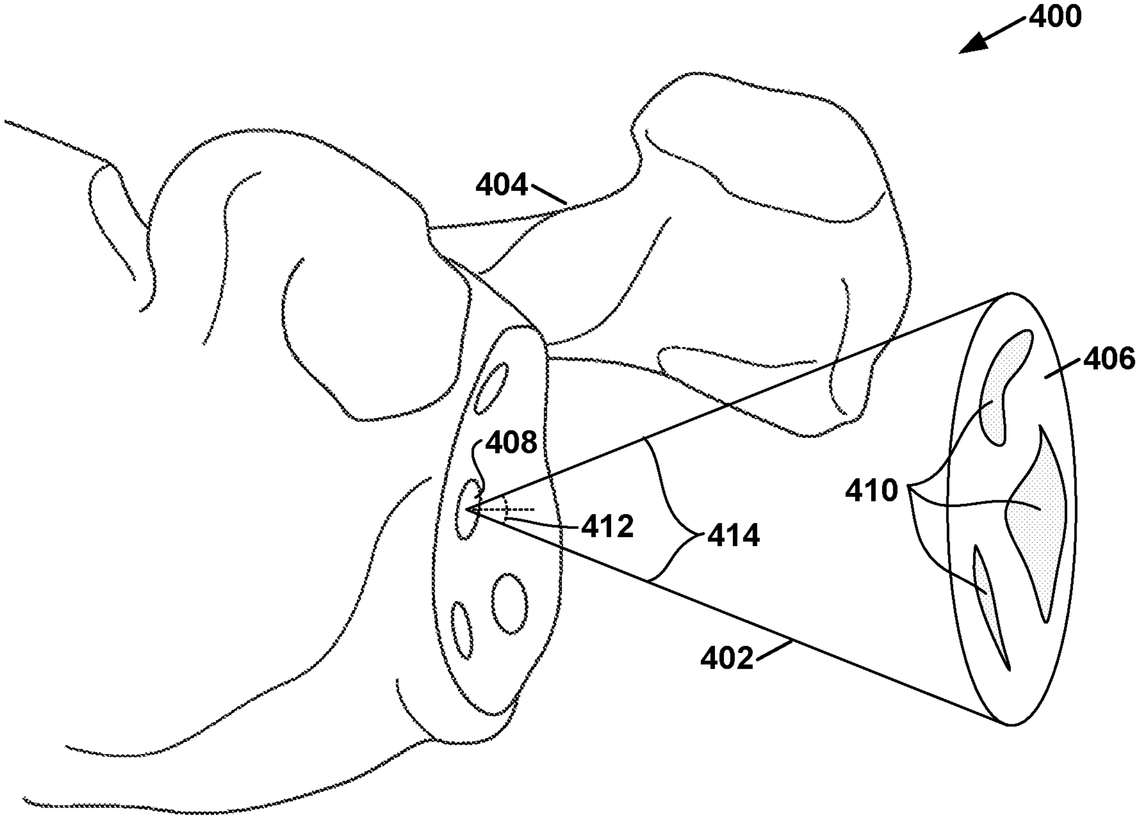
FIG. 4A is a conceptual diagram illustrating an example MR scene that includes a cone-shaped virtual trajectory guide that may help a user insert a surgical item into a bone, in accordance with one or more techniques of this disclosure.

FIG. 4A is a conceptual diagram illustrating an example MR scene 400 that includes a cone-shaped virtual trajectory guide 402 that may help a user insert a surgical item into a bone 404, in accordance with one or more techniques of this disclosure. In the example of FIG. 4A, surgical planning system 116 (FIG. 1) may cause MR visualization device 112 to present virtual trajectory guide 402 with respect to a bone 404. In the example of FIG. 4A, bone 404 is a scapula. In other examples, MR visualization device 112 may present virtual trajectory guide 402 with respect to other types of bones, such as the humerus, hip bone, femur, tibia, fibula, calcaneus, talus, and so on.

Virtual trajectory guide 402 is a virtual object (i.e., an object that does not exist in the real world). However, a user may be able to see virtual trajectory guide 402 along with parts of the real-world bone 404. In some examples, MR scene 400 may include other virtual objects and the user may be able to see other parts of the real world. In some examples, such as examples where the user is performing preoperative planning, rather than bone 404 being a real-world bone, bone 404 may be a virtual model of a bone of a patient.

In some examples where bone 404 is a real-world bone, surgical planning system 116 performs a registration process that registers bone 404 with virtual trajectory guide 402. Thus, virtual trajectory guide 402 may appear to the user to be at a fixed location relative to the bone. To perform the registration process, surgical planning system 116 may perform a SLAM algorithm that generates a map of the user's real-world environment. Furthermore, as part of performing the registration process, surgical planning system 116 determines a transformation that maps points in the map of the user's real-world environment to points on a set of one or more virtual objects. Various algorithms for determining such a transformation are known in the art.

In the example of FIG. 4A, virtual trajectory guide 402 includes an elliptical surface 406. A border of elliptical surface 406 may be elliptical. For instance, the border of elliptical surface 406 may be a circular or non-circular ellipse. In some examples, elliptical surface 406 is 2-dimensional. In other examples, elliptical surface 406 is convex or concave.

Elliptical surface 406 may include a plurality of locations. For example, elliptical surface 406 may be divided into a grid. In this example, each cell or a subset of cells in the grid may correspond to a different one of the locations. In some examples, the locations may cover all or a sub-region of elliptical surface 406.

For each location of the plurality of locations on elliptical surface 406, the location corresponds to a potential insertion axis that passes through the location and a potential insertion point 408 on the surface of bone 404. The location may be visually distinguished (e.g., color-coded) based on a quality of a portion of bone 404 along the potential insertion axis corresponding to the location. For example, the location may be blue-colored to indicate poor bone quality, yellow-colored to indicate medium bone quality, or green-colored to indicate good bone quality. In other examples, different shades of gray or different types of crosshatching may visually distinguish locations based on the quality of the portion of bone 404 along the potential insertion axis corresponding to the location. Thus, as shown in the example of FIG. 4A, different regions 410 of elliptical surface 406 are differently colored.

In some examples, one or more locations on elliptical surface 406 may indicate potential insertion axes that are not usable because the corresponding potential insertion axes intersect the planned or actual paths of other screws or other non-bone objects. For instance, if surgical planning system 116 has received an indication of user input indicating a selected insertion axis for a first screw, locations corresponding to potential insertion axes for a second that intersect the selected insertion axis for the first screw may be marked in elliptical surface 406. For instance, surgical planning system 116 may use a specific color to mark the locations on elliptical surface 406 corresponding to potential insertion axes that intersect the selected insertion axis for the first screw. In this way, the user may know to avoid using such potential insertion axes.

Furthermore, in some instances, bone 404 may already include another screw or other non-bone object. Surgical planning system 116 may mark locations on elliptical surface 406 corresponding to potential insertion axes that intersect the other screw or non-bone object in elliptical surface 406. For instance, surgical planning system 116 may use a specific color to mark the locations on elliptical surface 406 corresponding to potential insertion axes that intersect the other screw or non-bone object. In this way, the user may know to avoid using such potential insertion axes.

In some examples, there may be sensitive structures within on close to bone 404 that should not be damaged by insertion of a screw, drill bit, or other object. For example, an important nerve or blood vessel may run along an outer surface of bone 404 roughly opposite potential insertion point 408. While it is typically not recommended that a drill bit or self-tapping screw punch through the outer surface of bone 404 opposite potential insertion point 408, this is an event that may occur. Accordingly, surgical planning system 116 may mark locations on elliptical surface 406 corresponding to potential insertion axes that intersect (or come within a threshold minimum distance) of one or more sensitive structures. For instance, surgical planning system 116 may use a specific color to mark the locations on elliptical surface 406 corresponding to potential insertion axes that intersect (or come within a threshold minimum distance) of one or more sensitive structures. In this way, the user may know to avoid using such potential insertion axes.

In the example of FIG. 4A, virtual trajectory guide 402 is a cone-shaped 3D virtual object. Surgical planning system 116 positions an apex of the cone-shaped 3D virtual object at potential insertion point 408 on the surface of bone 404. As shown in the example of FIG. 4A, an angle 412 defined by the apex may correspond to a range of angles at which a screw is insertable through a screw hole into bone 404 during the surgical procedure, where the screw hole is defined by an orthopedic prosthesis to be attached to bone 404 during the surgical procedure. In some examples, for each location of the plurality of locations on elliptical surface 406, an angle of the potential insertion axis corresponding to the location relative to an axis orthogonal to the surface of bone 404 at potential insertion point 408 is within a range of angles at which the screw is insertable through the screw hole into bone 404 during the surgical procedure. Thus, outer edges 414 of virtual trajectory guide 402 may correspond to maximum angles at which a screw may be inserted through the screw hole into bone 404. In some examples, surgical planning system 116 may determine the range of angles for each screw hole of an orthopedic prosthesis based on data about the orthopedic prosthesis stored or retrieved by surgical planning system 116.

The user may use the differently colored regions 410 of elliptical surface 406 as a guide for inserting a drill bit into bone 404. For example, the user may position a drill bit so that a tip of the drill bit is at potential insertion point 408 and a part of the drill bit that intersects elliptical surface 406 is within a region (e.g., one of regions 410) that is associated with good bone quality. In this example, the user may then use a drill to insert the drill bit into bone 404 while keeping the drill bit within the region associated with good bone quality. After drilling a hole in this way, the user may insert a screw or pin into the resulting hole. Similarly, the user may use the differently colored regions 410 of elliptical surface 406 as a guide for inserting a self-tapping screw into bone 404. For example, the user may position a self-tapping screw so that a tip of the self-tapping screw is at potential insertion point 408 and a part of the self-tapping screw that intersects elliptical surface 406 is within a region (e.g., one of regions 410) that is associated with good bone quality. In this example, the user may then use a tool, such as a screwdriver or drill to insert the self-tapping screw into bone 404 while keeping the self-tapping screw within the region associated with good bone quality.

Figure 4B:
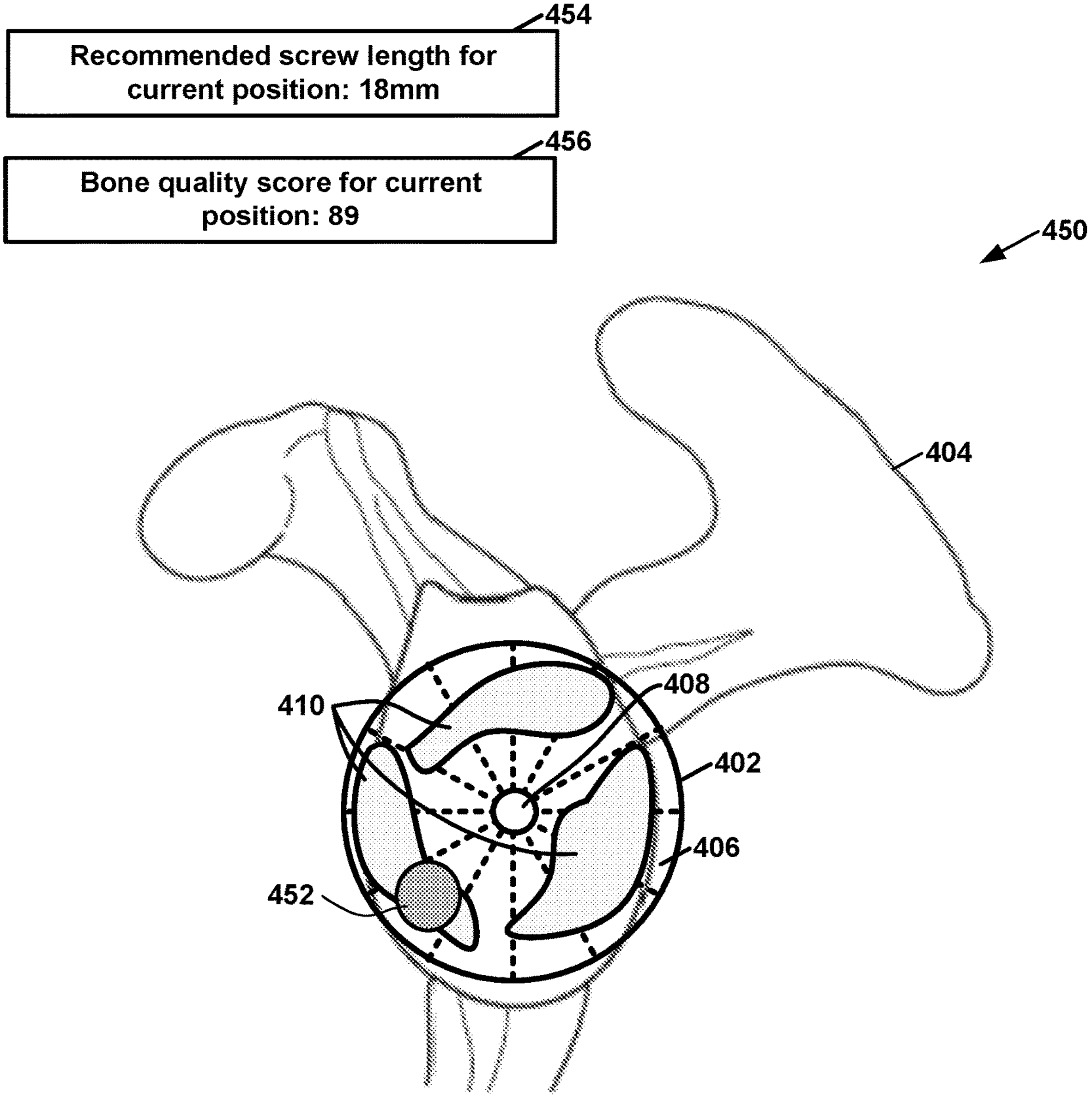
FIG. 4B is a conceptual diagram illustrating an example MR scene that includes a virtual trajectory guide of FIG. 4A from a different angle, in accordance with one or more techniques of this disclosure.

FIG. 4B is a conceptual diagram illustrating an example MR scene 450 that includes a cone-shaped virtual trajectory guide 402 of FIG. 4A from a different angle, in accordance with one or more techniques of this disclosure. In the example of FIG. 4B, MR scene 450 is rotated 90° degrees relative to MR scene 400 of FIG. 4A.

Furthermore, in some examples, surgical assistance system 100 may track a current position 452 of a user-controlled indicator within elliptical surface 406 of virtual trajectory guide 402. For instance, the user-controlled indicator may be a drill bit, a screwdriver, a cursor, a finger of the user, or another type of real or virtual object controlled by the user to indicate current position 452. In one example, the user-controlled indicator may include a drill bit positioned so that a tip of the drill bit is at the screw hole location on the surface of the bone. Surgical assistance system 100 may then determine a current location of the plurality of locations within elliptical surface 406 of virtual trajectory guide 402, where the current location corresponds to current position 452 of the user-controlled indicator. MR visualization device 112 may present, during the surgical procedure, a screw length indicator 454 for the current location. The screw length indicator 454 for the current location indicates a recommended length of a screw to insert along the potential insertion axis corresponding to the current location. In the example of FIG. 4B, the recommended screw length for the current position is 18 mm. Screw length indicator 454 may be a virtual object that is visible to the user or other user but does not exist in the real world.

As noted above, surgical assistance system 100 may determine the recommended length of the screw. In one example, surgical assistance system 100 may determine the recommended length of the screw by calculating a distance from the insertion point to a point that is a given distance (e.g., a given number of millimeters) from an outer surface of the cortical bone opposite the insertion point along the potential insertion axis. In this example, surgical assistance system 100 may calculate the distance based on medical images (e.g., x-rays, computed tomography (CT) scans, etc.) of the bone. Furthermore, in this example, surgical assistance system 100 may determine the recommended screw length as a screw length closest to the calculated distance or a next available screw length shorter than the calculated distance.

In some examples, MR visualization device 112 may present, during the surgical procedure, a bone quality indicator 456 for the current location. Bone quality indicator 456 for the current location indicates a bone quality metric of the bone along the potential insertion axis corresponding to the current location. Bone quality indicator 456 may be a virtual object that is visible to the user or other user but does not exist in the real world. MR visualization device 112 may update bone quality indicator 456 in response to user inputs to change the current position 452 of the user-controlled indicator.

Figure 5:
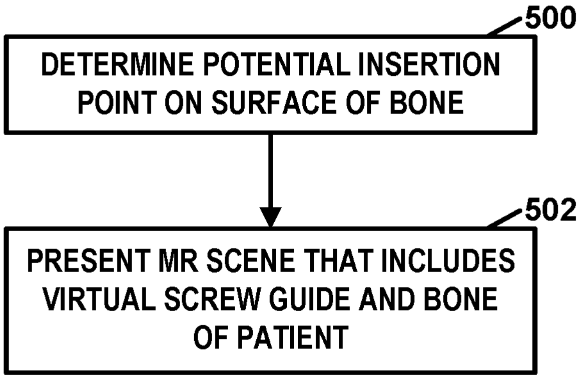
FIG. 5 is a flowchart illustrating an example operation of a surgical assistance system for presenting a virtual trajectory guide, in accordance with one or more techniques of this disclosure.

FIG. 5 is a flowchart illustrating an example operation of a surgical assistance system 100 for presenting virtual trajectory guide 402, in accordance with one or more techniques of this disclosure. The operation of FIG. 5 may be performed during a preoperative planning phase of a surgical procedure or during an intraoperative phase of the surgical procedure. In the example of FIG. 5, surgical assistance system 100 may determine a potential insertion point on a surface of a bone (500). In some examples, surgical assistance system 100 may determine the potential insertion point based on previously defined data in a surgical plan for the surgical procedure. In some examples, surgical assistance system 100 may determine the potential insertion point as a point indicated by a user input received by surgical assistance system 100. In some examples, the potential insertion point corresponds to a screw hole defined in an orthopedic prosthesis that is to be attached to the bone during the surgical procedure. In such examples, a surgical plan for the surgical procedure may specify a position of the orthopedic prosthesis relative to the bone. In some examples, surgical assistance system 100 may establish a position of the orthopedic prosthesis relative to the bone based on user input (e.g., user input to position a virtual model of the orthopedic prosthesis).

MR visualization device 112 of surgical assistance system 100 may present an MR scene that includes virtual trajectory guide 402 (502). The virtual trajectory guide includes an elliptical surface 406. For each location of a plurality of locations on elliptical surface 406, the location corresponds to a potential insertion axis that passes through the location and the potential insertion point on the surface of the bone. The location may be visually distinguished (e.g., color-coded) based on a quality of a portion of the bone along the potential insertion axis corresponding to the location. In some examples, MR visualization device 112 presents the MR scene during a surgical procedure. In some examples, MR visualization device 112 presents the MR scene during a planning phase of the surgical procedure.

Figure 6:
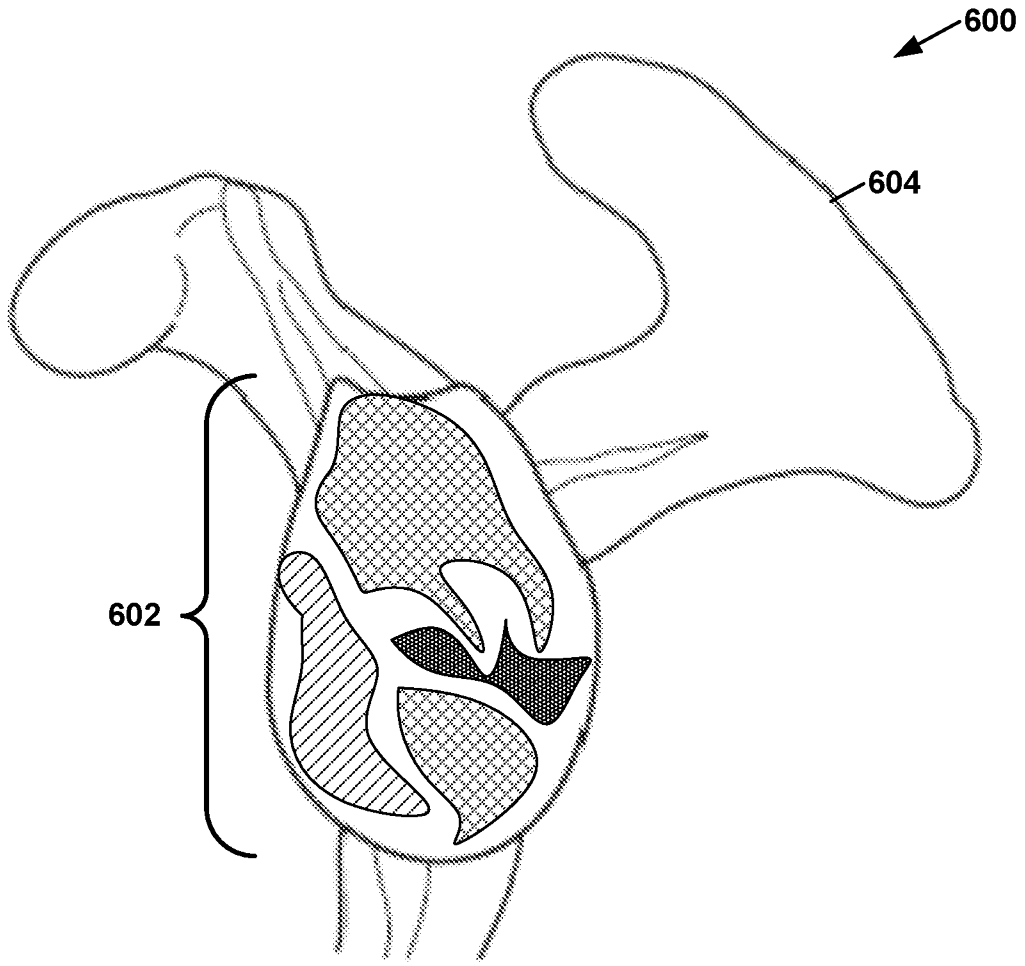
FIG. 6 is a conceptual diagram illustrating an example MR scene that includes a virtual bone quality map superimposed on a bone of a patient, in accordance with one or more techniques of this disclosure.

FIG. 6 is a conceptual diagram illustrating an example MR scene 600 that includes a virtual bone quality map 602 superimposed on a bone 604 of a patient, in accordance with one or more techniques of this disclosure. Unlike elliptical surface 406 of virtual trajectory guide 402, virtual bone quality map 602 may appear to a user of MR visualization device 112 to be applied to or "painted onto" a surface of bone 604, instead of floating some distance away from the surface of bone 604. Because the surface of bone 604 may have a 3-dimensional shape, virtual bone quality map 602 may also have a 3-dimensional shape matching the 3-dimensional shape of the surface of bone 604. In the example of FIG. 6, bone 604 is a scapula and the surface of bone 604 is a glenoid fossa of the scapula. In other examples, virtual bone quality map 602 may be applied to other types of bones. In some examples, such as during preoperative planning, bone 604 may be a virtual model of a bone.

Virtual bone quality map 602 may include a plurality of locations. For example, virtual bone quality map 602 may be divided into a grid. In this example, each cell or a subset of cells in the grid may correspond to a different one of the locations. In some examples, the locations may cover all or a sub-region of virtual bone quality map 602.

For each respective location in a plurality of locations on virtual bone quality map 602, the respective location indicates a bone quality of bone 604 along a potential insertion axis corresponding to the respective location. The potential insertion axis corresponding to the respective location passes through bone 604 and the respective location. In some examples, for some or all of the locations, the potential insertion axes corresponding to the locations are at angles orthogonal to a surface of bone 604 at the locations. In other words, for any such location, the corresponding potential insertion axis intersects the surface of bone 604 at right angles.

In other examples, for some or all of the locations on virtual bone quality map 602, the potential insertion axes corresponding to the locations are at orientations corresponding to highest bone quality. For instance, for a given location, surgical assistance system 100 may search for an orientation within a range of orientations that has a highest bone quality score. Thus, in such examples, virtual bone quality map 602 may indicate the highest bone quality for any potential insertion axis within the range of orientations passing through the locations. In other words, for at least one location in the plurality of locations, the insertion axis corresponding to the location is at an orientation corresponding to highest bone quality among a set of potential insertion axes passing through the potential insertion point.

Virtual bone quality map 602 may indicate the bone quality of a location in one or more ways. For example, virtual bone quality map 602 may indicate the bone quality of a location based on a visual distinguishing system (e.g., a color-coding system). For example, the location may be blue-colored to indicate poor bone quality, yellow-colored to indicate medium bone quality, or green-colored to indicate good bone quality. In some examples, virtual bone quality map 602 may indicate the bone quality of a location as a numerical value. For instance, in such examples, virtual bone quality map 602 may indicate the bone quality of a location on a scale of 1-10. In the example of FIG. 6, virtual bone quality map 602 indicates the bone quality of location as different cross-hatching patterns.

A user may use virtual bone quality map 602 to determine where to place screws, pins, or other surgical items into bone 604, e.g., during or before performing a surgical procedure. Use of virtual bone quality map 602 during a surgical procedure may be especially helpful to a user in situations in which bone 604 is not in the same condition as expected during a planning phase of the surgical procedure. For example, the surgical procedure may be a revision surgery in which an existing orthopedic prosthesis is detached from bone 604. Detaching an existing orthopedic prosthesis from bone 604 may remove certain parts of bone 604 in unpredictable ways. In other examples, bone 604 may simply have aspects that are not understood during the planning phase of the surgical procedure. Thus, the user may need to be able to adapt to the changed circumstances. Surgical planning system 116 may determine an updated shape of bone 604 by using depth images captured during the surgical procedure to generate a partial intra-operative model of bone 604 and merging the intra-operative model of bone 604 with a pre-surgical model of bone 604 to generate an intra-operative model of bone 604. In this example, surgical assistance system 100 may calculate bone quality based on the intra-operative model of bone 604.

As discussed above with respect to FIG. 4A, there is the possibility that specific potential insertion axes intersect a planned or insertion axis of another screw, intersect an existing screw or non-bone structure, intersect or come within a minimum threshold distance of a sensitive structure, or should not be used for some other reason. Accordingly, in the example of FIG. 6, virtual bone quality map 602 may indicate locations corresponding to such potential insertion axes. For instance, surgical planning system 116 may use a specific color on virtual bone quality map 602 to indicate locations corresponding to such potential insertion axes.

Figure 7A:
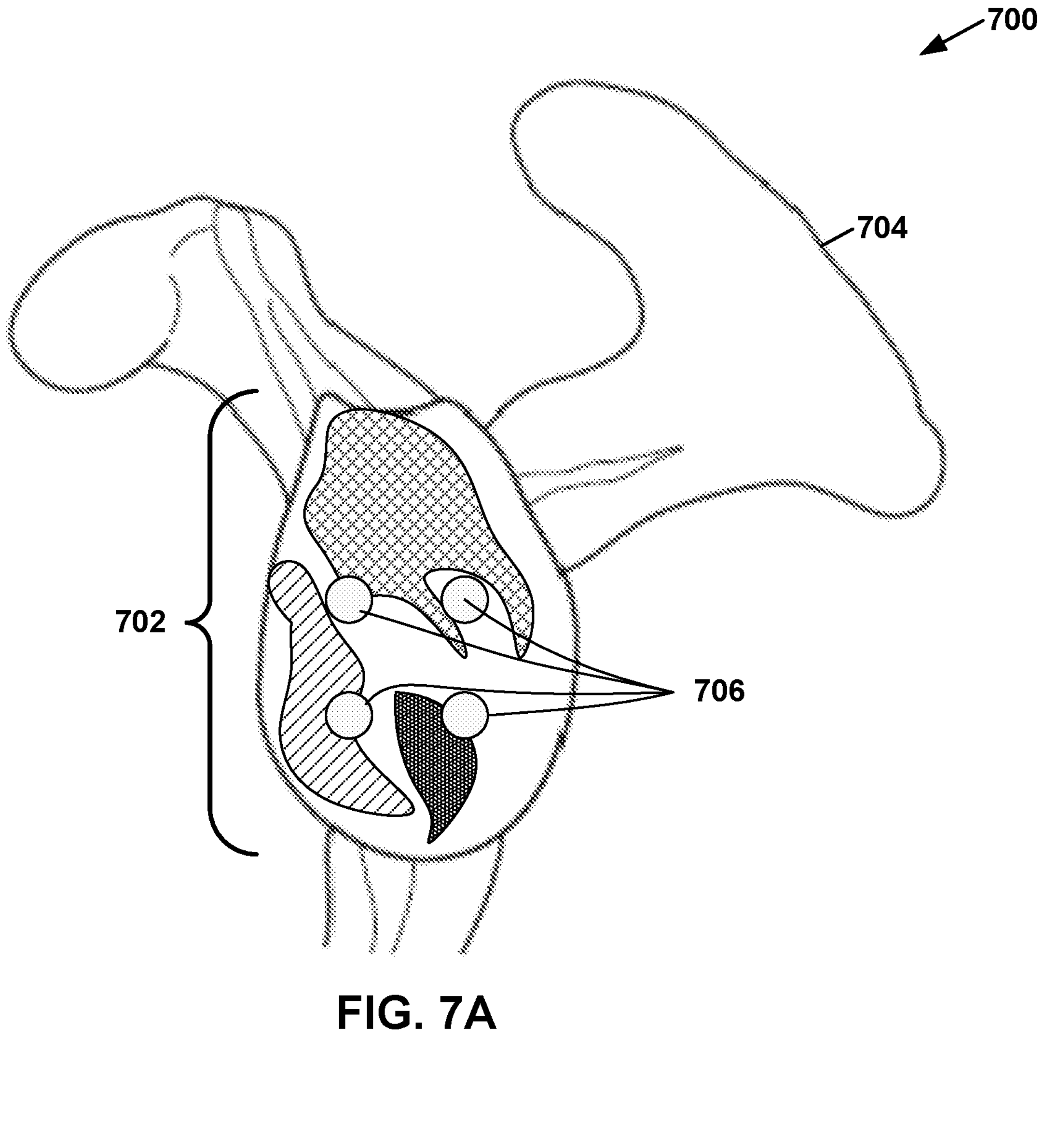
FIG. 7A is a conceptual diagram illustrating an example MR scene that includes a virtual bone quality map superimposed on a bone of a patient along with virtual screw hole markers, in accordance with one or more techniques of this disclosure.

FIG. 7A is a conceptual diagram illustrating an example MR scene 700 that includes a virtual bone quality map 702 superimposed on a bone 704 of a patient along with virtual insertion point markers 706, in accordance with one or more techniques of this disclosure. In the example of FIG. 7A, the description provided elsewhere in this disclosure with respect to virtual bone quality map 602 (FIG. 6) may apply with respect to virtual bone quality map 702. Virtual insertion point markers 706 may have a fixed spatial relationship to one another and may correspond to screw holes defined by an orthopedic prosthesis to be attached to bone 704. Thus, virtual insertion point markers 706 may indicate to the user where screws inserted through screw holes defined in the orthopedic prosthesis would enter bone 704. In some examples, such as during preoperative planning, bone 704 may be a virtual model of a bone.

By reviewing virtual insertion point markers 706 with respect to virtual bone quality map 702, a user may be able to determine whether one or more of the screw holes are aligned with areas of good or bad bone quality. For example, the user may be able to quickly determine based on MR scene 700 that a screw entering bone 704 at a point corresponding to the bottom-right virtual insertion point marker 706 would enter an area of poor bone quality, assuming that the darkest cross-hatching in FIG. 7A corresponds to poor bone quality. The user can then plan accordingly.

Figure 7B:
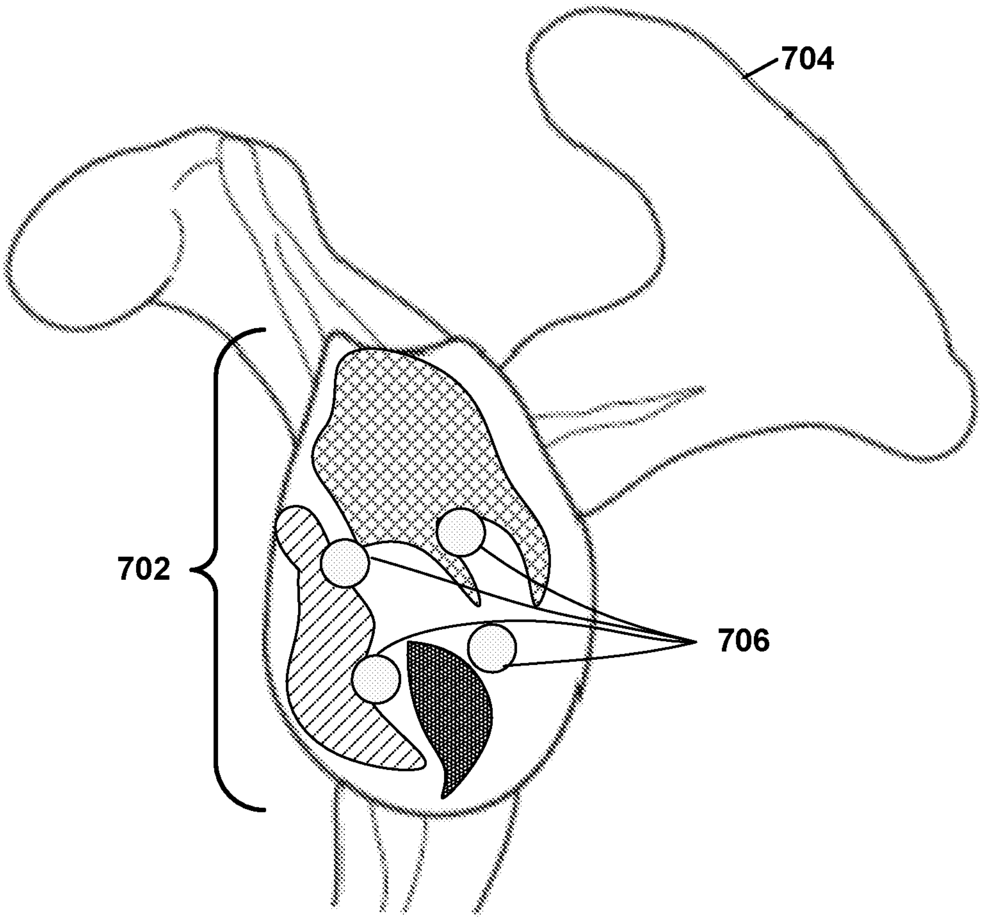
FIG. 7B is a conceptual diagram illustrating an example in which the MR scene of FIG. 7A includes a virtual bone quality map superimposed on a bone of a patient along with rotated virtual screw hole markers, in accordance with one or more techniques of this disclosure.

In some examples, one or more of the virtual insertion point markers 706 corresponds to an insertion point for a pin used during the surgical procedure. Thus FIG. 7B is a conceptual diagram illustrating an example in which the MR scene 700 of FIG. 7A includes virtual bone quality map 702 superimposed on bone 704 of a patient along with rotated virtual insertion point markers 706, in accordance with one or more techniques of this disclosure. As noted above, a user may be able to use virtual bone quality map 702 to determine whether one or more of the screw holes of an orthopedic prosthesis are aligned with areas of good or bad bone quality.

In accordance with one or more techniques of this disclosure, surgical planning system 116 may determine, at least one of a translation or rotation of virtual insertion point markers 706 relative to virtual bone quality map 702 to increase bone quality along axes passing through the virtual insertion point markers 706 relative to a current set of positions of virtual insertion point markers 706. Additionally, surgical planning system 116 may cause MR visualization device 112 to present virtual insertion point markers 706 after application of the translation and/or rotation of virtual insertion point markers 706. Thus, as shown in the example of FIG. 7B, virtual insertion point markers 706 are rotated relative to the positions of virtual insertion point markers 706 as shown in FIG. 7A. In some examples, surgical planning system 116 causes MR visualization device 112 to present virtual insertion point markers 706 during an inter-operative phase of the surgical procedure. In some examples, surgical planning system 116 causes MR visualization device 112 to present virtual insertion point markers 706 during a planning phase of the surgical procedure.

Surgical planning system 116 may determine how to rotate or translate the virtual insertion point markers 706 in one of a variety of ways. For example, the bone quality of the locations within virtual bone quality map 702 may correspond to numerical values. In this example, surgical assistance system 100 may perform a search over combinations of rotations and translations to identify a combination of a rotation and/or a translation that results in a highest total numerical value. The search may be constrained to combinations of rotations and translations that do not result in loss of range of movement and would not make the orthopedic prosthesis unusable. In some examples, the search may be constrained to combinations of rotations and translations that do not result in potential insertion axes that intersect planned insertion axes for other screws, locations of existing screws or other non-bone objects, intersect or come within a minimum threshold distance of a sensitive structure, or otherwise should not be used.

In some examples, surgical planning system 116 may rotate or translate the virtual insertion point markers 706 relative to virtual bone quality map 702 and bone 704 in response to receiving one or more indications of user input.

For example, surgical planning system 116 may rotate or translate virtual insertion point markers 706 in response to receiving indication of a twisting or sliding gesture of the user's hand. In another example, surgical planning system 116 may rotate or translate virtual insertion point markers 706 in response to receiving an indication or mouse input, keyboard input, or voice input. There may be limits on the degrees to which the orthopedic prosthesis may be rotated or translated without impairing the patient's range of motion or without being becoming unusable. Accordingly, surgical planning system 116 may automatically limit the degrees to which the user may rotate or translate virtual insertion point markers 706.

The user may be able to select better positions for the screw holes of the orthopedic prosthesis by reviewing translated or rotated virtual insertion point markers 706 relative to virtual bone quality map 702 and bone 704. For instance, in the example of FIG. 7B, after rotation of virtual insertion point markers 706, the bottom-right virtual screw hole marker is no longer within the darkest cross-hatched region, which corresponds to poor bone quality.

Figure 7C:
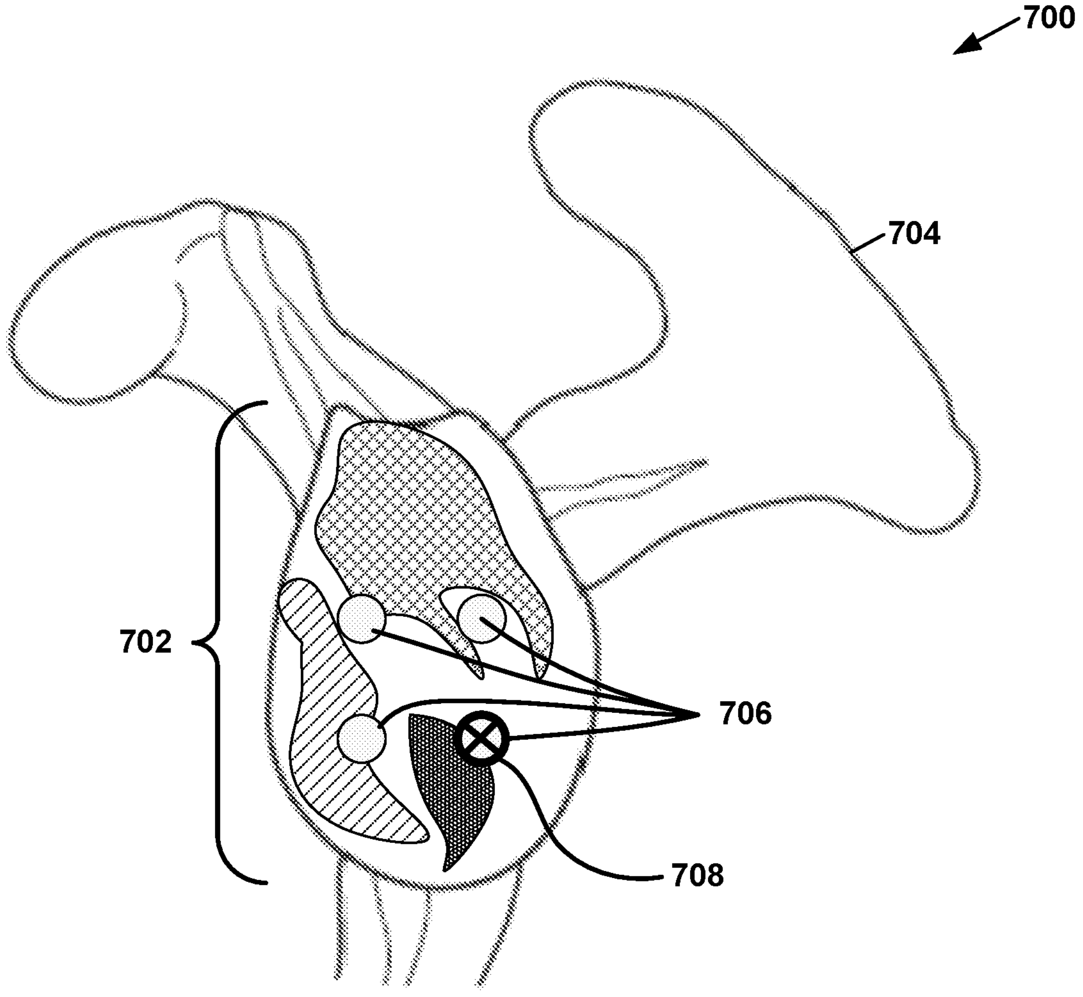
FIG. 7C is a conceptual diagram illustrating an example in which the MR scene of FIG. 7A includes a virtual bone quality map superimposed on a bone of a patient along with virtual screw hole markers including a non-recommended virtual screw hole marker, in accordance with one or more techniques of this disclosure.

FIG. 7C is a conceptual diagram illustrating an example in which the MR scene 700 of FIG. 7A includes virtual bone quality map 702 superimposed on bone 704 of a patient along with virtual insertion point markers 706 including a non-recommended virtual screw hole marker 708, in accordance with one or more techniques of this disclosure. In some examples, it may not be necessary to use all available screw holes defined in an orthopedic prosthesis to adequately attach the orthopedic prosthesis to a bone. For example, an orthopedic prosthesis may define four screw holes, but it may only be necessary to use three of the screw holes in order to adequately secure the orthopedic prosthesis to the bone.

Hence, in accordance with a technique of this disclosure, surgical assistance system 100 may determine, based on the bone quality of bone 704, that use of a subset of the screw holes corresponding to the virtual insertion point markers is unnecessary for attaching the orthopedic prosthesis to the bone. Additionally, MR visualization device 112 of surgical assistance system 100 may present, during the surgical procedure, an indication that use of the subset of the screw holes corresponding to the virtual insertion point markers is unnecessary for attaching the orthopedic prosthesis to the bone. For instance, in the example of FIG. 7C, the bottom-right virtual insertion point marker 706 is shown with an X to indicate that it may be unnecessary to use the screw hole corresponding to the bottom-right virtual screw hole indicator when attaching the orthopedic prosthesis to bone 704.

Surgical planning system 116 may determine that use of a subset of the screw holes corresponding to the virtual insertion point markers is unnecessary for attaching the orthopedic prosthesis to the bone in one of several ways. For instance, in one example, surgical planning system 116 may determine that only a specific number of the screw holes defined by the orthopedic prosthesis are needed for adequately attaching the orthopedic prosthesis to the bone. In this example, surgical planning system 116 may make this determination based on information from the manufacturer of the orthopedic prosthesis, information from the user, or information from another source. In this example, surgical planning system 116 may also determine which of the screw holes are aligned with the best bone quality up to the specific number of screw holes and mark one or more of the remaining screw holes of the orthopedic prosthesis as non-recommended.

Furthermore, in one example, surgical planning system 116 may determine that only specific screw holes defined by the orthopedic prosthesis are needed for adequately attaching the orthopedic prosthesis to the bone. In this example, surgical planning system 116 may make this determination based on information from the manufacturer of the orthopedic prosthesis, information from the user, or information from another source. Furthermore, in this example, surgical planning system 116 determine whether any of the screw holes that are defined by the orthopedic prosthesis and are determined to be unneeded for adequately attaching the orthopedic prosthesis to the bone are aligned with regions of poor bone quality. In this example, surgical planning system 116 may mark such screw holes of the orthopedic prosthesis as non-recommended.

Figure 8:
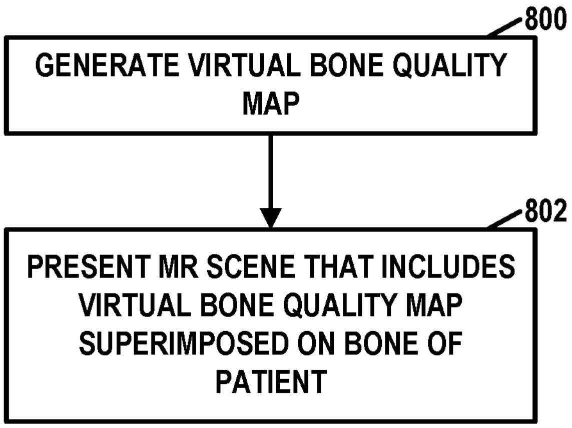
FIG. 8 is a flowchart illustrating an example operation of a surgical assistance system for presenting an MR scene that includes a virtual bone quality map, in accordance with one or more techniques of this disclosure.

FIG. 8 is a flowchart illustrating an example operation of surgical assistance system 100 for presenting an MR scene that includes a bone quality map, in accordance with one or more techniques of this disclosure. The operation of FIG. 8 may be performed during a preoperative planning phase of a surgical procedure or an intraoperative phase of the surgical procedure. In the example of FIG. 8, surgical planning system 116 of surgical assistance system 100 may generate a virtual bone quality map, such as virtual bone quality map 602 (FIG. 6) or virtual bone quality map 702 (FIGS. 7A-7C) (800). Surgical assistance system 100 may generate the virtual bone quality map in one of a variety of ways. For example, surgical planning system 116 may obtain a set of CT images of a bone, such as bone 604 (FIG. 6) or bone 704 (FIGS. 7A-7C). Each of the CT images of the bone corresponds to a 2-dimensional slice of the bone. Furthermore, for each of the CT images of the bone, surgical planning system 116 may partition the CT image into a set of regions and determine a map of Hounsfield unit values for the regions. In general, higher Hounsfield unit values correspond with greater bone density. Hence, cortical bone may have higher Hounsfield unit values than cancellous bone. Surgical planning system 116 may determine a 3D model of at least a relevant part of the bone by layering the maps of Hounsfield unit values. Thus, there may be a Hounsfield unit value for each voxel (3-dimensional position) in the 3D model. Surgical planning system 116 may then use the 3D model to determine bone quality values for locations on a surface of the bone.

For instance, in an example where the bone quality value for a location on the surface of the bone corresponds to a bone quality of the bone along a potential insertion axis orthogonal to the surface of the bone at the location, surgical planning system 116 may determine the bone quality value for the location based on Hounsfield unit values of voxels intersected by the potential insertion axis. For instance, surgical planning system 116 may determine the bone quality value for the location as a sum of Hounsfield unit values of the voxels intersected by the potential insertion axis. In another instance, surgical planning system 116 may determine the bone quality value for the location as a sum of Hounsfield unit values of values intersected by the potential insertion axis that are above a specific threshold (e.g., so as to exclude voxels corresponding to cancellous bone).

In examples where the bone quality value for a location corresponds to a highest bone quality of the bone in a plurality of potential insertion axes (e.g., potential insertion axes that are possible through a screw hole defined by an orthopedic prosthesis), surgical assistance system 100 may calculate bone quality values for each of the potential insertion axes as described in the previous example and select a highest bone quality value as the bone quality value for the location.

Additionally, in the example of FIG. 8, MR visualization device 112 of surgical assistance system 100 may present an MR scene that includes the virtual bone quality map superimposed on the bone of the patient or a virtual model of the bone (802). For example, MR visualization device 112 may superimpose the virtual bone quality map on the real-world bone during performance of the surgical procedure. MR visualization device 112 may superimpose the virtual bone quality map on a virtual model of the bone during a planning phase of the surgical procedure.

For each respective location in a plurality of locations on virtual bone quality map 702, the respective location indicates a bone quality of bone 704 along a potential insertion axis corresponding to the respective location. The potential insertion axis corresponding to the respective location passes through bone 704 and the respective location.

Figure 9A:
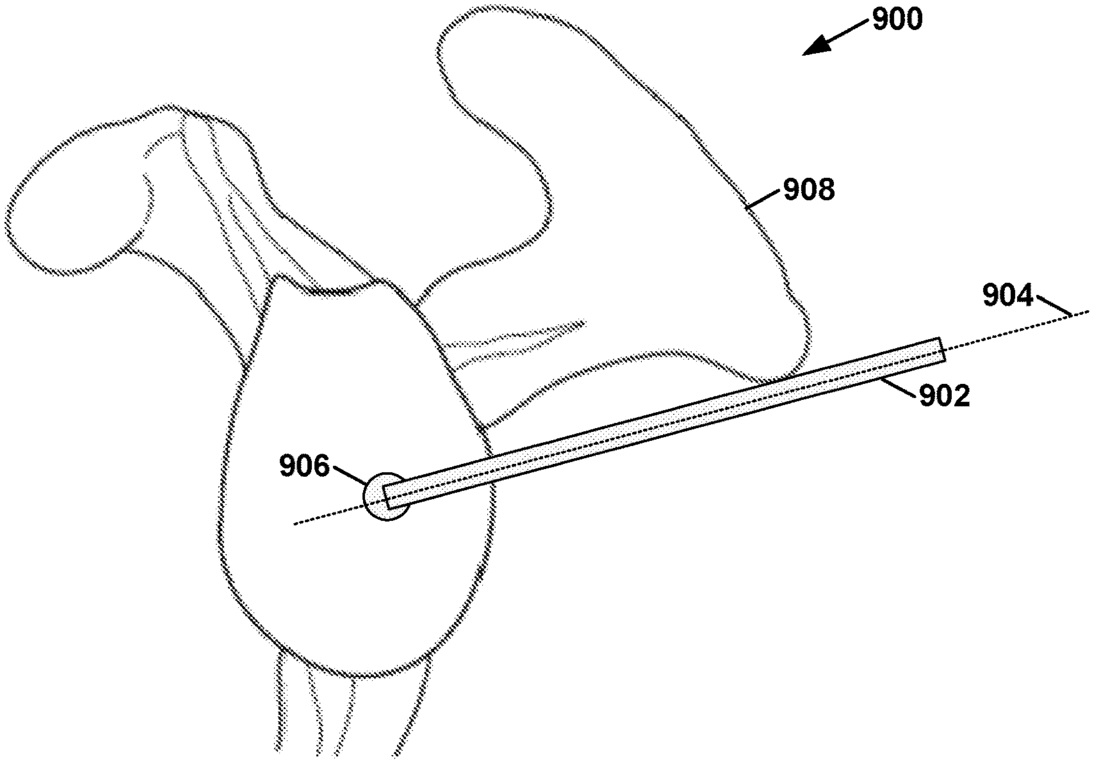
FIG. 9A is a conceptual diagram illustrating an example MR scene that includes a virtual insertion axis object, in accordance with one or more techniques of this disclosure.
Figure 9B:
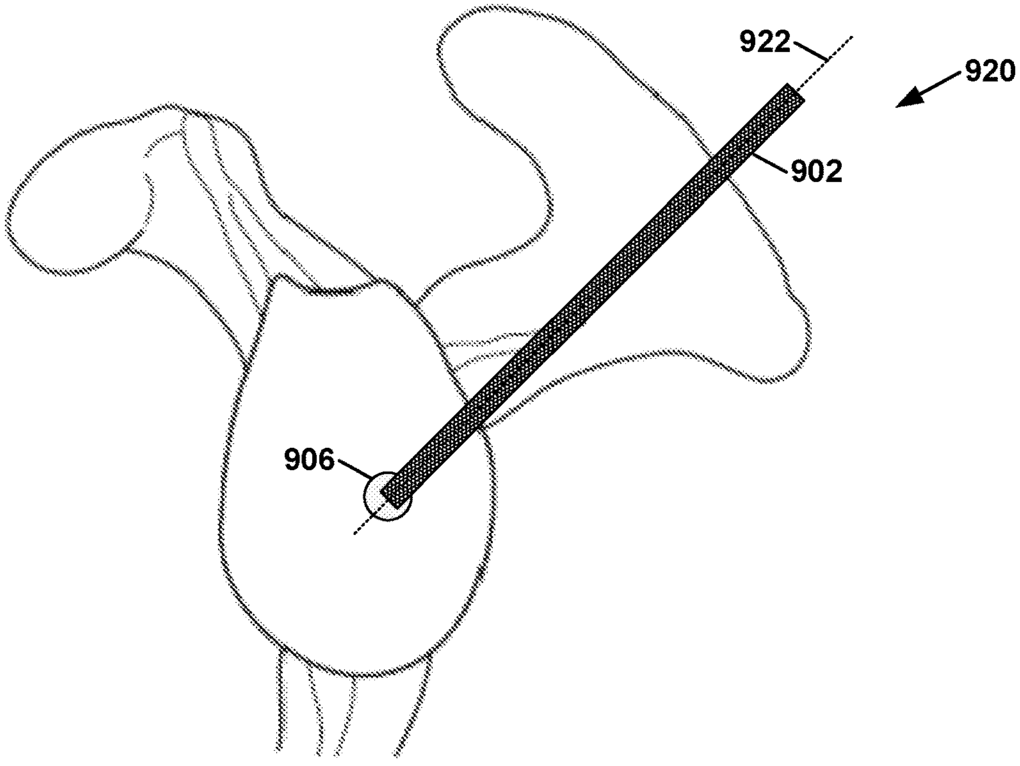
FIG. 9B is a conceptual diagram illustrating an example MR scene that include the virtual insertion axis object of FIG. 9A oriented at a different angle, in accordance with one or more techniques of this disclosure.

FIG. 9A is a conceptual diagram illustrating an example MR scene 900 that includes a virtual insertion axis object 902, in accordance with one or more techniques of this disclosure. In the example of FIG. 9A, virtual insertion axis object 902 is aligned along an axis 904 that that intersects a potential insertion point 906 on a bone 908 of a patient and has a first orientation. In some examples, such as during preoperative planning, bone 908 may be a virtual model of a bone. Virtual insertion axis object 902 may represent a line along which a user may insert a screw, drill bit, pin, or other object into bone 908. Potential insertion point 906 may represent a point at which the user inserts the screw, drill bit, pin, or other object into bone 908. Although FIGS. 9A and 9B show bone 908 as being a scapula, the techniques of this disclosure may be applied with respect to other types of bones.

Surgical planning system 116 may receive an indication of user input to change an orientation of virtual insertion axis object 902 relative to a surface of bone 908 from the first orientation to a second orientation. Surgical planning system 116 may receive the indication of user input in one or more ways. For instance, in one example, a user may hold a drill so that a tip of a drill bit attached to the drill is located at potential insertion point 906. In this example, surgical planning system 116 may maintain an alignment between virtual insertion axis object 902 and the drill bit. Hence, in this example, receiving the indication of user input to change the orientation of virtual insertion axis object 902 may include surgical planning system 116 detecting a movement of the drill bit having a tip located at potential insertion point 906 from a first orientation to a second orientation. In another example, surgical planning system 116 may detect that the user has performed a grasping hand gesture to virtually grasp virtual insertion axis object 902 and a dragging hand gesture to reorient virtual insertion axis object 902. In another example, surgical planning system 116 may receive voice commands instructing surgical planning system 116 how to reorient virtual insertion axis object 902. For instance, in this example, surgical planning system 116 may receive a voice command instructing surgical planning system 116 to reorient virtual insertion axis object 902 object a given number of degrees in a given direction. In other examples, surgical planning system 116 may receive the indication of user input via a keyboard or touch-sensitive surface.

In response to receiving the indication of user input, surgical planning system 116 may cause MR visualization device 112 to update a position of virtual insertion axis object 902 so that virtual insertion axis object 902 is aligned along a second axis that intersects potential insertion point 906 on bone 908 and has the second orientation. Additionally, in response to receiving the indication of user input, surgical planning system 116 may provide user feedback with respect to a bone quality of the bone along the second axis.

In some examples, surgical planning system 116 may prevent the user from reorienting virtual insertion axis object 902 beyond a range of angles through which a screw may be inserted through a screw hole defined by an orthopedic prosthesis that is to be attached to the bone during the surgical procedure. In other words, surgical planning system 116 may make it so that the user cannot reorient virtual insertion axis object 902 so that virtual insertion axis object 902 has an orientation that a screw passing through a screw hole of an orthopedic prosthesis cannot have.

FIG. 9B is a conceptual diagram illustrating an example MR scene 920 that includes virtual insertion axis object of FIG. 9A oriented at a different angle, in accordance with one or more techniques of this disclosure. In the example of FIG. 9B, virtual insertion axis object 902 is aligned along a second axis 922 that intersects potential insertion point 906 on bone 908. Second axis 922 has a different orientation from axis 904 of FIG. 9A.

Surgical assistance system 100 may provide user feedback with respect to the bone quality of bone 908 along axis 922. For instance, in the example of FIG. 9A and FIG. 9B, MR visualization device 112 may update a color of virtual insertion axis object 902 based on the bone quality of bone 908 along axis 922. Specifically, in the example of FIG. 9A and FIG. 9B, MR visualization device 112 may update the color of virtual insertion axis object 902 from a lighter color to a darker color based on the bone quality of bone 908 along axis 922 as opposed to axis 904. In other examples, MR visualization device 112 may update the color of virtual insertion axis object 902 along a spectrum of colors according to bone quality.

In some examples, providing the user feedback may include providing at least one of audible or tactile feedback based on the bone quality of bone 908 along axis 922. For instance, a speaker of surgical assistance system 100 (e.g., a speaker of MR visualization device 112) may output higher-pitched or more frequent beeps when there is higher bone quality along an axis of virtual insertion axis object 902 than when there is lower bone quality along the axis of virtual insertion axis object 902. In another example, a speaker of surgical assistance system 100 (e.g., a speaker of MR visualization device 112) may output voice indications of the bone quality along the axis of virtual insertion axis object 902. In some examples where the user is using a drill or other elongated object to explore the bone quality along different axes through potential insertion point 906 and surgical planning system 116 may update an orientation of virtual insertion axis object 902 based on an orientation of a drill bit of the drill, surgical planning system 116 may cause a haptic feedback unit of the drill to vibrate with greater intensity when there is poorer bone quality along an axis of the drill bit and to vibrate with less intensity when there is better bone quality along the axis of the drill bit.

Furthermore, in some examples, the user feedback may provide information about whether the axis of virtual insertion axis object 902 intersects a previously planned insertion axis of another screw or object, intersects an existing screw or other non-bone object, intersects or comes within a minimum threshold distance of a sensitive structure, or otherwise should not be used. For example, a specific color, sound, pattern of haptic feedback may indicate when the axis of virtual insertion axis object 902 intersects a previously planned insertion axis of another screw or object, intersects an existing screw or other non-bone object, intersects or comes within a minimum threshold distance of a sensitive structure, or otherwise should not be used.

In some examples, surgical assistance system 100 may determine, in response to receiving the indication of user input, a recommended screw length for a screw to be inserted into bone 908. Additionally, MR visualization device 112 may provide a virtual recommended screw length indicator in an MR scene (e.g., MR scene 900 or MR scene 920). The virtual recommended screw length indicator indicates the recommended screw length. The virtual recommended screw length indicator may resemble screw length indicator 454 of FIG. 4B. Surgical assistance system 100 may determine the recommended screw length in accordance with any of the examples provided above with respect to FIG. 4B and elsewhere in this disclosure. Thus, as the user provides user input to change the orientation of virtual insertion axis object 902, surgical assistance system 100 may provide the user with updated recommended screw lengths. This may help the user decide which angle to use when inserting an object into the bone. Moreover, similar to the example of FIG. 4B, MR scene 900 and/or MR scene 920 may include a bone quality indicator similar to bone quality indicator 456 of FIG. 4B.

Furthermore, in some examples, surgical planning system 116 may receive an indication of user input to change a position of the virtual insertion axis object so that virtual insertion axis object 902 is aligned along an axis that intersects a different potential insertion point on bone 908 of the patient. In response to receiving the indication of this user input, surgical planning system 116 may cause MR visualization device 112 to update the position of virtual insertion axis object 902 so that virtual insertion axis object 902 is aligned along an axis that intersects the different potential insertion point on bone 908 of the patient. Additionally, surgical assistance system 100 may provide user feedback with respect to a bone quality of bone 908 along the axis that intersects the different potential insertion point on bone 908 of the patient. In this way, the user may be able to evaluate bone quality at different potential insertion points.

Figure 10:
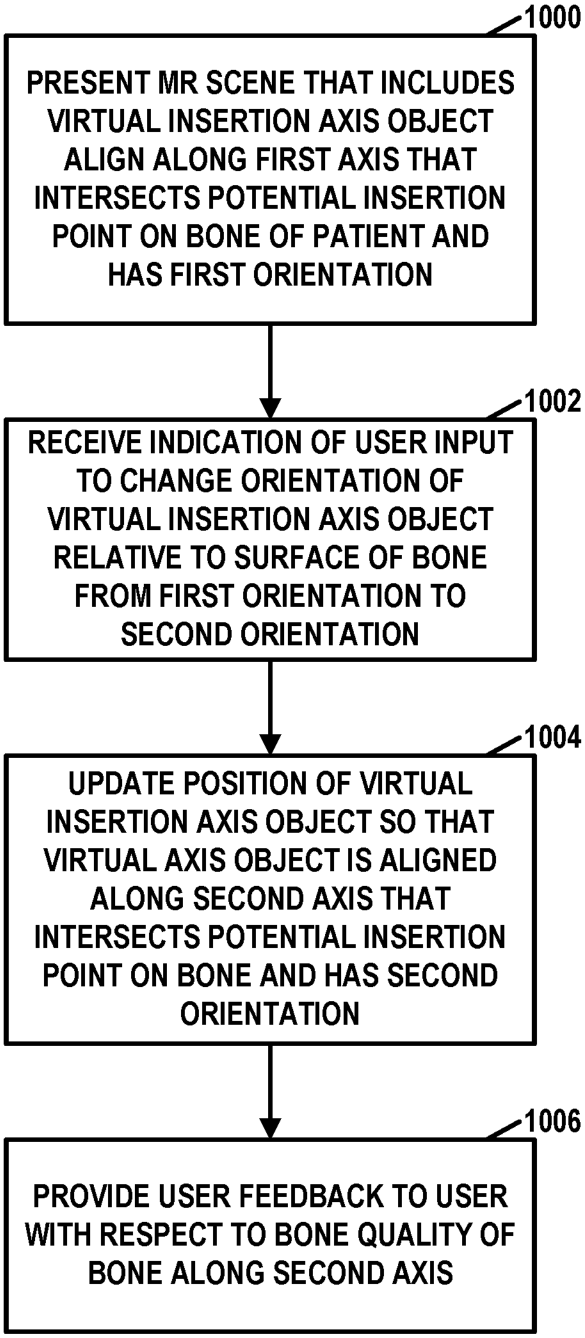
FIG. 10 is a flowchart illustrating an example operation of the surgical assistance system for presenting a virtual insertion axis object, in accordance with one or more techniques of this disclosure.

FIG. 10 is a flowchart illustrating an example operation of surgical assistance system 100 for presenting a virtual insertion axis object, such a virtual insertion axis object 902 (FIG. 9A, FIG. 9B), in accordance with one or more techniques of this disclosure. The example operation of FIG. 10 may be performed during a preoperative planning phase of a surgical procedure or during an intraoperative phase of the surgical procedure.

As shown in the example of FIG. 10, surgical planning system 116 may cause MR visualization device 112 to present an MR scene (e.g., MR scene 900) that includes the virtual insertion axis object aligned along a first axis that intersects a potential insertion point (e.g., potential insertion point 906) on a bone (e.g., bone 908) of the patient and has a first orientation (1000). Surgical planning system 116 may receive an indication of user input to change an orientation of the virtual insertion axis object relative to a surface of the bone from the first orientation to a second orientation (1002). Surgical planning system 116 may receive the indication of user input in accordance with any of the examples provided elsewhere in this disclosure.

In response to receiving the indication of user input, surgical planning system 116 may cause MR visualization device 112 to update a position of the virtual insertion axis object so that the virtual insertion axis object is aligned along a second axis that intersects the potential insertion point on the bone and has the second orientation (1004). Additionally, in response to receiving the indication of user input, surgical assistance system 100 may provide user feedback with respect to a bone quality of the bone along the second axis (1006).

The following is a non-limiting list of examples that may be in accordance with one or more techniques of this disclosure.

Example 1A. A method comprising: determining, by a surgical assistance system, a potential insertion point on a surface of a bone of a patient; and presenting, by a Mixed Reality (MR) visualization device of the surgical assistance system, an MR scene that includes a virtual trajectory guide, wherein: the virtual trajectory guide comprises an elliptical surface, and for each location of a plurality of locations on the elliptical surface: the location corresponds to a potential insertion axis that passes through the location and the potential insertion point on the surface of the bone, and the location is visually distinguished based on a quality of a portion of the bone along the potential insertion axis corresponding to the location.

Example 2A. The method of example 1A, wherein the potential insertion point corresponds to a screw hole defined in an orthopedic prosthesis that is to be attached to the bone during the surgical procedure.

Example 3A. The method of example 2A, wherein, for each location of the plurality of locations on the elliptical surface, an angle of the insertion axis corresponding to the location relative to an axis orthogonal to the surface of the bone at the potential insertion point is within a range of angles at which a screw is insertable through the screw hole into the bone during the surgical procedure.

Example 4A. The method of any of examples 2A-3A, wherein: the virtual trajectory guide is a cone-shaped 3-dimensional (3D) virtual object, presenting the MR scene comprises positioning, by the surgical assistance system, an apex of the cone-shaped 3D virtual object at the potential insertion point on the surface of the bone, and an angle defined by the apex corresponds to a range of angles at which a screw is insertable through the screw hole into the bone during the surgical procedure.

Example 5A. The method of any of examples 1A-4A, further comprising: tracking, by the surgical assistance system, a current position of a user-controlled indicator within the elliptical surface of the virtual trajectory guide; determining, by the surgical assistance system, a current location of the plurality of locations within the elliptical surface of the virtual trajectory guide, wherein the current location corresponds to the current position of the user-controlled indicator; and presenting, by the MR visualization device during the surgical procedure, a screw length indicator for the current location, wherein the screw length indicator for the current location indicates a recommended length of a screw to insert along the potential insertion axis corresponding to the current location.

Example 6A. The method of any of examples 1A-5A, further comprising: tracking, by the surgical assistance system, a current position of a user-controlled indicator within the elliptical surface of the virtual screw guide; determining, by the surgical assistance system, a current location of the plurality of locations within the elliptical surface of the virtual screw guide, wherein the current location corresponds to the current position of the user-controlled indicator; and presenting, by the MR visualization device during the surgical procedure, a bone quality indicator for the current location, wherein the bone quality indicator for the current location indicates a bone quality metric of the bone along the screw insertion axis corresponding to the current location.

Example 7A. The method of any of examples 5A-6A, wherein the user-controlled indicator comprises a drill bit positioned so that a tip of the drill bit is at the potential insertion point on the surface of the bone.

Example 8A. The method of any of examples 1A-7A, wherein presenting the MR scene comprises presenting, by the MR visualization device, the MR scene during a surgical procedure.

Example 1B. A method comprising: generating, by a surgical assistance system, a virtual bone quality map, wherein for each respective location in a plurality of locations on the virtual bone quality map: the respective location indicates a bone quality of a bone along a potential insertion axis corresponding to the respective location, and the potential insertion axis corresponding to the respective location passes through the bone and the respective location; and presenting, by a Mixed Reality (MR) visualization device of the surgical assistance system, an MR scene that includes the virtual bone quality map superimposed on a bone of the patient or a virtual model of the bone of the patient.

Example 2B. The method of example 1B, wherein, for at least one location in the plurality of locations, the potential insertion axis corresponding to the location is at an angle orthogonal to a surface of the bone at the location.

Example 3B. The method of any of examples 1B-2B, wherein, for at least one location in the plurality of locations, the potential insertion axis corresponding to the location is at an orientation corresponding to a highest bone quality among a set of potential insertion axes passing through the potential insertion point.

Example 4B. The method of any of examples 1B-3B, wherein presenting the MR scene further comprises: including, by the MR visualization device, in the MR scene, a set of one or more virtual insertion point markers superimposed on the bone quality map, wherein locations of the virtual insertion point markers correspond to screw holes defined in an orthopedic prosthesis to be attached to the bone during the surgical procedure.

Example 5B. The method of example 4B, further comprising: determining, by the surgical assistance system, at least one of a translation or rotation of the virtual insertion point markers relative to the bone quality map to increase bone quality along axes passing through the virtual insertion point markers relative to a current set of positions of the virtual insertion point markers; and presenting, by the MR visualization device during the surgical procedure, the virtual insertion point markers after application of the translation and/or rotation of the virtual insertion point markers.

Example 6B. The method of any of examples 4B-5B, further comprising: determining, by the surgical assistance system based on bone quality of the bone, that use of a subset of the screw holes corresponding to the virtual insertion point markers is unnecessary for attaching the orthopedic prosthesis to the bone; and presenting, by the MR visualization device during the surgical procedure, an indication that use of the subset of the screw holes corresponding to the virtual insertion point markers is unnecessary for attaching the orthopedic prosthesis to the bone Example 7B. The method of any of examples 1B-6B, wherein presenting the MR scene further comprises: including, by the MR visualization device, in the MR scene, a virtual insertion point marker superimposed on the bone quality map, wherein a location of the virtual insertion point corresponds to an insertion point for a pin used during the surgical procedure.

Example 8B. The method of any of examples 1B-7B, wherein presenting the MR scene comprises presenting, by the MR visualization device, the MR scene during a surgical procedure.

Example 1C. A method comprising: presenting, by a MR visualization device of a surgical assistance system, an MR scene that includes a virtual insertion axis object aligned along a first axis that intersects a potential insertion point on a bone of a patient and has a first orientation; receiving, by the surgical assistance system, an indication of user input to change an orientation of the virtual insertion axis object relative to a surface of the bone from the first orientation to the second orientation; and in response to receiving the indication of user input: updating, by the MR visualization device, a position of the virtual insertion axis object so that the virtual insertion axis object is aligned along a second axis that intersects the potential insertion point on the bone and has the second orientation; and providing, by the surgical assistance system, user feedback with respect to a bone quality of the bone along the second axis.

Example 2C. The method of example 1C, wherein providing the user feedback comprises updating, by the MR visualization device, a color of the virtual insertion axis object based on the bone quality of the bone along the second axis.

Example 3C. The method of any of examples 1C-2C, wherein providing the user feedback comprises providing, by the surgical assistance system, at least one of audible or tactile feedback based on the bone quality of the bone along the second axis.

Example 4C. The method of any of examples 1C-3C, further comprising, in response to receiving the indication of user input: determining, by the surgical assistance system, a recommended screw length for a screw to be inserted along the second axis; and providing, by the MR visualization device, a virtual recommended screw length indicator in the MR scene, wherein the virtual recommended screw length indicator indicates the recommended screw length.

Example 5C. The method of any of examples 1C-4C, wherein receiving the indication of user input to change the angle of the virtual insertion axis object comprises: detecting, by the surgical assistance system, a movement of a drill bit having a tip located at the potential insertion point from the first orientation to the second orientation.

Example 6C. The method of any of examples 1C-5C, wherein: the user input is a first user input, the potential insertion point is a first potential insertion point, the user feedback is first user feedback, and the method further comprises: receiving, by the surgical assistance system, an indication of second user input to change a position of the virtual insertion axis object so that the virtual insertion axis object is aligned along a third axis that intersects a second potential insertion point on the bone of the patient, wherein the second potential insertion point is different from the first potential insertion point; and in response to receiving the indication of second user input: updating, by the MR visualization device, the position of the virtual insertion axis object so that the virtual insertion axis object is aligned along the third axis that intersects the second potential insertion point on the bone of the patient; and providing, by the surgical assistance system, second user feedback with respect to a bone quality of the bone along the third axis that intersects the second potential insertion point on the bone of the patient.

Example 7C. The method of any of examples 1C-6C, wherein presenting the MR scene comprises presenting, by the MR visualization device, the MR scene during a surgical procedure.

Example 1D. A method comprising any combination of the methods of examples 1A-7C.

Example 2D. A computer-readable storage medium having instructions stored thereon that, when executed, configure a surgical assistance system to perform the methods of any of examples 1A-7C.

Example 3D. A surgical assistance system comprising means for performing the methods of any of examples 1A-7C.

Example 4D. Any combination of examples 1A-7C.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention. Moreover, techniques of this disclosure have generally been described with respect to human anatomy. However, the techniques of this disclosure may also be applied to animal anatomy in veterinary cases.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuity," as used herein may refer to any of the foregoing structures or any other structure suitable for implementation of the techniques described herein.

Various examples have been described. These and other examples are within the scope of the following claims.

What is claimed is:

1. A method comprising:

determining, by a surgical assistance system, a potential insertion point on a surface of a bone of a patient; and presenting, by a Mixed Reality (MR) visualization device of the surgical assistance system, an MR scene that includes a virtual trajectory guide, wherein:

the virtual trajectory guide comprises a 3-dimensional (3D) virtual object comprising an elliptical surface and an apex, wherein presenting the MR scene comprises positioning the apex of the 3D virtual object at the potential insertion point on the surface of the bone, and wherein an angle defined by the apex of the 3D virtual object corresponds to a range of angles at which a screw is insertable into the bone through a screw hole defined by an orthopedic prosthesis, and for each location of a plurality of locations on the elliptical surface of the 3D virtual object:

the location corresponds to a potential insertion axis that passes through the location and the potential insertion point on the surface of the bone, wherein an angle of the potential insertion axis is within the range of angles at which the screw is insertable into the bone through the screw hole, and the location is visually distinguished in the elliptical surface from one or more other locations on the elliptical surface based on a quality of a portion of the bone along the potential insertion axis corresponding to the location.

2. The method of claim 1, wherein the orthopedic prosthesis is to be attached to the bone during a surgical procedure.

3. The method of claim 1, wherein the angle of the potential insertion axis corresponding to the location comprises an angle relative to an axis orthogonal to the surface of the bone at the potential insertion point and is within the range of angles at which the screw is insertable into the bone through the screw hole during a surgical procedure.

4. The method of claim 2, wherein:

the 3D virtual object is a cone-shaped 3-dimensional (3D) virtual object.

5. The method of claim 1, further comprising:

tracking, by the surgical assistance system, a current position of a user-controlled indicator within the elliptical surface;

determining, by the surgical assistance system, a current location of the plurality of locations within the elliptical surface, wherein the current location corresponds to the current position of the user-controlled indicator; and presenting, by the MR visualization device during a surgical procedure, a screw length indicator for the current location, wherein the screw length indicator for the current location indicates a recommended length of a screw to insert along a potential insertion axis corresponding to the current location.

6. The method of claim 1, further comprising:

tracking, by the surgical assistance system, a current position of a user-controlled indicator within the elliptical surface;

determining, by the surgical assistance system, a current location of the plurality of locations within the elliptical surface, wherein the current location corresponds to the current position of the user-controlled indicator; and presenting, by the MR visualization device during a surgical procedure, a bone quality indicator for the current location, wherein the bone quality indicator for the current location indicates a bone quality metric of the bone along a potential insertion axis corresponding to the current location.

7. The method of claim 5, wherein the user-controlled indicator comprises a drill bit positioned so that a tip of the drill bit is at the potential insertion point on the surface of the bone.

8. The method of claim 1, wherein presenting the MR scene comprises presenting, by the MR visualization device, the MR scene during a surgical procedure.

9. The method of claim 1, further comprising:

generating, by the surgical assistance system, a virtual bone quality map, wherein for each respective location in a plurality of locations on the virtual bone quality map:

the respective location indicates a bone quality of the bone along a potential insertion axis corresponding to the respective location on the virtual bone quality map, and the potential insertion axis corresponding to the respective location on the virtual bone quality map passes through the bone and the respective location on the virtual bone quality map; and presenting, by the MR visualization device, a second MR scene that includes the virtual bone quality map superimposed on the bone or a virtual model of the bone.

10. The method of claim 9, wherein, for at least one location in the plurality of locations on the virtual bone quality map, a potential insertion axis corresponding to the at least one location on the virtual bone quality map is at an angle orthogonal to the surface of the bone at the location.

11. The method of claim 9, wherein, for at least one location in the plurality of locations on the virtual bone quality map, a potential insertion axis corresponding to the at least one location on the virtual bone quality map is at an orientation corresponding to a highest bone quality among a set of potential insertion axes passing through the potential insertion point.

12. The method of claim 9, wherein presenting the second MR scene further comprises:

including, by the MR visualization device, in the second MR scene, a set of one or more virtual insertion point markers superimposed on the virtual bone quality map, wherein locations of the virtual insertion point markers correspond to screw holes defined in the orthopedic prosthesis.

13. The method of claim 12, further comprising:

determining, by the surgical assistance system, at least one of a translation or rotation of the virtual insertion point markers relative to the virtual bone quality map to increase bone quality along axes passing through the virtual insertion point markers relative to a current set of positions of the virtual insertion point markers; and presenting, by the MR visualization device during a surgical procedure, the virtual insertion point markers after application of at least one of the translation or rotation of the virtual insertion point markers.

14. The method of claim 12, further comprising:

determining, by the surgical assistance system based on bone quality of the bone, that use of a subset of the screw holes corresponding to the virtual insertion point markers is unnecessary for attaching the orthopedic prosthesis to the bone; and presenting, by the MR visualization device during a surgical procedure, an indication that use of the subset of the screw holes corresponding to the virtual insertion point markers is unnecessary for attaching the orthopedic prosthesis to the bone.

15. The method of claim 9, wherein presenting the second MR scene further comprises:

including, by the MR visualization device, in the second MR scene, a virtual insertion point marker superimposed on the virtual bone quality map, wherein a location of the virtual insertion point marker corresponds to an insertion point for a pin used during a surgical procedure.

16. The method of claim 9, wherein presenting the second MR scene comprises presenting, by the MR visualization device, the second MR scene during a surgical procedure.

17. The method of claim 1:

presenting, by the MR visualization device, a second MR scene that includes a virtual insertion axis object aligned along a first axis that intersects the potential insertion point on the surface of the bone and has a first orientation;

receiving, by the surgical assistance system, an indication of user input to change an orientation of the virtual insertion axis object relative to the surface of the bone from the first orientation to a second orientation; and in response to receiving the indication of the user input:

updating, by the MR visualization device, a position of the virtual insertion axis object so that the virtual insertion axis object is aligned along a second axis that intersects the potential insertion point on the surface of the bone and has the second orientation; and providing, by the surgical assistance system, user feedback with respect to a bone quality of the bone along the second axis.

18. The method of claim 17, wherein providing the user feedback comprises updating, by the MR visualization device, a color of the virtual insertion axis object based on the bone quality of the bone along the second axis.

19. The method of claim 17, wherein providing the user feedback comprises providing, by the surgical assistance system, at least one of audible or tactile feedback based on the bone quality of the bone along the second axis.

20. The method of claim 17, further comprising, in response to receiving the indication of the user input:

determining, by the surgical assistance system, a recommended screw length for a screw to be inserted along the second axis; and providing, by the MR visualization device, a virtual recommended screw length indicator in the second MR scene, wherein the virtual recommended screw length indicator indicates the recommended screw length.

21. The method of claim 17, wherein receiving the indication of the user input to change the orientation of the virtual insertion axis object comprises:

detecting, by the surgical assistance system, a movement of a drill bit having a tip located at the potential insertion point from the first orientation to the second orientation.

22. The method of claim 17, wherein:

the user input is a first user input, the potential insertion point is a first potential insertion point, the user feedback is first user feedback, and the method further comprises:

receiving, by the surgical assistance system, an indication of second user input to change a position of the virtual insertion axis object so that the virtual insertion axis object is aligned along a third axis that intersects a second potential insertion point on the surface of the bone, wherein the second potential insertion point is different from the first potential insertion point; and in response to receiving the indication of the second user input:

updating, by the MR visualization device, the position of the virtual insertion axis object so that the virtual insertion axis object is aligned along the third axis that intersects the second potential insertion point on the surface of the bone; and providing, by the surgical assistance system, second user feedback with respect to a bone quality of the bone along the third axis that intersects the second potential insertion point on the surface of the bone.

23. A non-transitory computer-readable storage medium having instructions stored thereon that, when executed, configure a surgical assistance system to:

determine a potential insertion point on a surface of a bone of a patient; and present, by a Mixed Reality (MR) visualization device of the surgical assistance system, an MR scene that includes a virtual trajectory guide, wherein:

the virtual trajectory guide comprises a 3-dimensional (3D) virtual object comprising an elliptical surface and an apex, wherein presenting the MR scene comprises positioning the apex of the 3D virtual object at the potential insertion point on the surface of the bone, and wherein an angle defined by the apex of the 3D virtual object corresponds to a range of angles at which a screw is insertable into the bone through a screw hole defined by an orthopedic prosthesis, and for each location of a plurality of locations on the elliptical surface of the 3D virtual object:

the location corresponds to a potential insertion axis that passes through the location and the potential insertion point on the surface of the bone, wherein the potential insertion axis corresponds to an angle of the range of angles at which the screw is insertable into the bone through the screw hole, and the location is visually distinguished in the elliptical surface from one or more other locations on the elliptical surface based on a quality of a portion of the bone along the potential insertion axis corresponding to the location.

24. A surgical assistance system comprising:

a Mixed Reality (MR) visualization device of the surgical assistance system, the MR visualization device configured to present an MR scene that includes a virtual trajectory guide, wherein:

the virtual trajectory guide comprises a 3-dimensional (3D) virtual object comprising an elliptical surface and an apex, wherein presenting the MR scene comprises positioning the apex of the 3D virtual object at a potential insertion point on a surface of a bone of a patient, and wherein an angle defined by the apex of the 3D virtual object corresponds to a range of angles at which a screw is insertable into the bone through a screw hole defined by an orthopedic prosthesis, and for each location of a plurality of locations on the elliptical surface of the 3D virtual object:

the location corresponds to a potential insertion axis that passes through the location and the potential insertion point on the surface of the bone, wherein an angle of the potential insertion axis is within the range of angles at which the screw is insertable into the bone through the screw hole, and the location is visually distinguished in the elliptical surface from one or more other locations on the elliptical surface based on a quality of a portion of the bone along the potential insertion axis corresponding to the location.

* * * * *